(12) United States Patent
Herpin et al.

(10) Patent No.: US 7,041,692 B2
(45) Date of Patent: May 9, 2006

(54) METHODS OF TREATING FACTOR VIIA-ASSOCIATED CONDITIONS WITH COMPOUNDS HAVING AN AMINE NUCLEUS

(75) Inventors: Timothy Herpin, Princeton, NJ (US); Gregory S. Bisacchi, Ringoes, NJ (US); Zulan Pi, Pennington, NJ (US); E. Scott Priestley, Yardley, PA (US); T. G. Murali Dhar, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 53 days.

(21) Appl. No.: 10/464,366

(22) Filed: Jun. 17, 2003

(65) Prior Publication Data

US 2004/0029940 A1    Feb. 12, 2004

Related U.S. Application Data

(60) Provisional application No. 60/389,833, filed on Jun. 19, 2002.

(51) Int. Cl.
- *A61K 31/42* (2006.01)
- *A61K 31/41* (2006.01)
- *A61K 31/415* (2006.01)

(52) U.S. Cl. .................. 514/374; 514/383; 514/400; 514/406

(58) Field of Classification Search ............. 514/374, 514/383, 400, 406
See application file for complete search history.

(56) References Cited

U.S. PATENT DOCUMENTS 5,023,236 A  *  6/1991  Edgington et al. ............ 514/18
6,399,773 B1     6/2002  Liu et al.

FOREIGN PATENT DOCUMENTS

WO      WO 96/20689       7/1996

* cited by examiner

*Primary Examiner*—Johann Richter
*Assistant Examiner*—Ebenezer Sackey
(74) *Attorney, Agent, or Firm*—Anastasia P. Winslow; Jing G. Sun

(57) ABSTRACT

Methods of treating Factor VIIa-associated conditions in a mammal are described, comprising administering to the mammal in need of treatment thereof an effective amount of at least one compound having the formula (I),

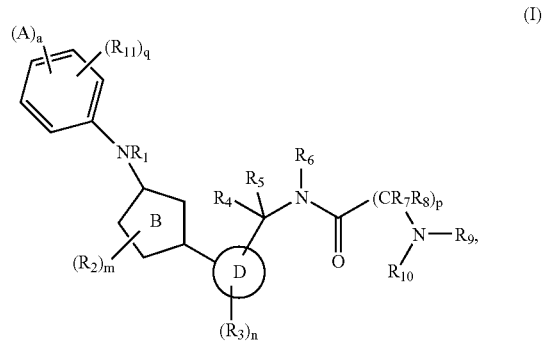

or a pharmaceutically-acceptable salt, hydrate or prodrug thereof.

14 Claims, No Drawings

METHODS OF TREATING FACTOR VIIA-ASSOCIATED CONDITIONS WITH COMPOUNDS HAVING AN AMINE NUCLEUS

CROSS-REFERENCE TO RELATED APPLICATIONS

The present application claims the priority benefit of U.S. Provisional Application No. 60/389,833, filed Jun. 19, 2002, which is expressly incorporated fully herein by reference.

FIELD OF THE INVENTION

The present invention relates to methods of treating conditions associated with the activity of Factor VIIa comprising administration of compounds having an amine nucleus, as further defined herein. The invention further relates to select compounds having surprisingly advantageous activity in inhibiting Factor VIIa.

BACKGROUND OF THE INVENTION

An elevated blood plasma level of Factor VIIa is a risk factor for cardiovascular disease and abnormalities of the coagulation system. Uncontrolled FVIIa activation can lead to occlusive arterial thrombosis and thromboembolism which can produce unstable angina, myocardial infarction, and stroke. It is estimated that this year 1.1 million Americans will have a new or secondary heart attack, and about one third of them will die. This makes arterial thrombotic diseases the single leading cause of death in America. Stroke killed an estimated 158,000 people in 1995 and is the third largest cause of death (ranking behind heart disease and all forms of cancer). Stroke is also the single leading cause of disability in the United States.

Thrombosis in the veins deep in thighs or calves (deep vein thrombosis) can lead to ischemia, pain, tenderness, and discoloration of the affected area. A major complication of venous thrombosis is pulmonary embolism, i.e., a clot breaks free and travels through the venous circulation and right heart to the pulmonary circulation, where it blocks an artery of the lung. Pulmonary function is compromised and death may follow. It is estimated that there are about 50,000 deaths per year resulting from pulmonary embolism (Moser, 1990).

FVIIa activation can also result from gram-negative bacteremia which causes half of the cases of lethal septic shock acquired during hospitalization. Bacterial lipopolysaccharide (LPS) and inflammatory mediators mediate some of the sequelae including a coagulopathy that may be triggered by expression of tissue factor (TF) on macrophages and endothelial cells.

Accordingly, antithrombotic agents have been researched and developed for use in treating cardiovascular and other diseases. Presently, antithrombotic agents include heparin, coumarin, and aspirin, among others. There are, however, limitations with these agents. For example, both heparin and coumarin have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding. Thrombin inhibitors and their drawbacks are further discussed in WO 96/20689 to duPont Merck Pharmaceutical Co.

As may be appreciated, those in the field of pharmaceutical research continue to seek to develop new compounds and compositions having increased effectiveness and bioavailability and/or having fewer side effects. There is particularly an interest in developing agents that can selectively and directly inhibit key factors in the complicated coagulation process. The present invention provides compounds useful as inhibitors of Factor VIIa. Amino-based compounds useful as IMPDH inhibitors are disclosed in U.S. Pat. No. 6,399,773, and compounds useful as IMPDH inhibitors and Factor VIIa inhibitors are disclosed in U.S. patent application Ser. No. 09/997,963, filed Nov. 29, 2001, a continuation-in-part application to U.S. patent application Ser. No. 09/428,432. Additionally, compounds useful in treating Factor VIIa conditions are described in U.S. provisional application Ser. No. 60/389,832, titled "Ureido-Substituted Aniline Compounds Useful As Serine Protease Inhibitors," filed Jun. 19, 2002, with common inventors herein and assigned to the present assignee. Each of the patents, patent applications, and articles cited herein are incorporated herein by reference.

SUMMARY OF THE INVENTION

The instant invention comprises methods of treating Factor VIIa-associated conditions in a mammal comprising administering to the mammal in need of treatment thereof, an effective amount of at least one compound having the formula (I),

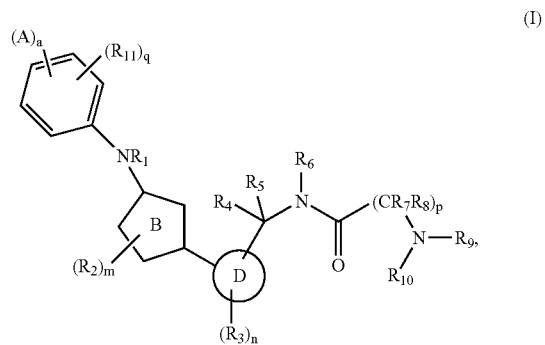

or a pharmaceutically-acceptable salt, hydrate or prodrug thereof, wherein:

A is a five or six-membered saturated or unsaturated carbocyclic, heterocyclic or heteroaryl ring, said ring A being optionally substituted with up to three groups selected from $R_{27}$;

B is selected from one of

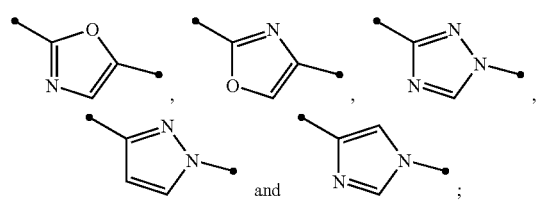

D is phenyl, cycloalkyl, or a five to six-membered heteroaryl or heterocyclo, provided, however, that when A is a heterocyclo or heteroaryl and a is 1, then D is phenyl or cycloalkyl;

$R_1$ is hydrogen, $C_{1-4}$alkyl, or $C_{1-4}$alkyl substituted with one to two $R_{21}$;

$R_2$ and $R_3$ are attached to any available carbon atom of ring B and ring D, respectively, and at each occurrence are independently selected from halogen, cyano, $NO_2$, $C_{1-6}$alkyl, substituted $C_{1-6}$alkyl, $C_{2-6}$alkenyl, $C_{2-6}$alkynyl, haloalkyl, haloalkoxy, $-OR_{15}$, $-C(=O)R_{15}$, $-OC(=O)R_{15}$, $-CO_2R_{15}$, $-OCO_2R_{15}$, $-C(=O)NR_{15}R_{16}$, $-OC(=O)NR_{15}R_{16}$, $-NR_{15}R_{16}$, $-NR_{16}C(=O)R_{15}$, $-NR_{16a}C(=O)NR_{15}R_{16}$, $-NR_{16}CO_2R_{15}$, $-SR_{15}$, $-S(O)R_{15}$, $-SO_2R_{15}$, $-SO_2NR_{15}R_{16}$, $-SO_3R_{15}$, $-NR_{16}SO_2R_{15}$, and $-NR_{16a}SO_2NR_{15}R_{16}$;

$R_4$ and $R_5$ are independently selected from hydrogen, halogen, hydroxy, cyano, $C_{1-3}$alkoxy, $-OCF_3$, $CF_3$, amino, $C_{1-6}$alkylamino, $C_{1-4}$alkyl, and $C_{1-4}$alkyl substituted with one to two $R_{22}$; or alternatively, $R_4$ and $R_5$ taken together may form a 3–8 membered cycloalkyl or heterocyclic spiro ring, said ring being optionally substituted with up to three $R_{28}$;

$R_6$ is hydrogen, $C_{1-4}$alkyl, or $C_{1-4}$alkyl substituted with one to two $R_{23}$;

$R_7$ and $R_8$ are independently selected from hydrogen, halogen, hydroxy, cyano, $C_{1-3}$alkoxy, $-OCF_3$, $CF_3$, amino, $C_{1-6}$alkylamino, $C_{1-4}$alkyl, and $C_{1-4}$alkyl substituted with one to two $R_{24}$; or alternatively, $R_7$ and $R_8$ taken together may form a 3–8 membered cycloalkyl or heterocyclic spiro ring, said ring being optionally substituted with up to three $R_{29}$; or alternatively, one or both of $R_7$ and $R_8$ may be taken together with one or both of $R_9$ and $R_{10}$ to form a heterocyclic or heteroaryl ring, said ring in turn being optionally substituted with up to three $R_{30}$;

$R_9$ and $R_{10}$ are independently selected from hydrogen, $C_{1-4}$alkyl, and $C_{1-4}$alkyl substituted with one to two $R_{25}$; or alternatively, $R_9$ and $R_{10}$ taken together may form a 3–8 membered heterocyclic ring or a five to six membered heteroaryl ring, said ring being optionally substituted with up to three $R_{30}$; or alternatively, one or both of $R_9$ and $R_{10}$ may be taken together with one or both of $R_7$ and $R_8$ to form a heterocyclic or heteroaryl ring, said ring being optionally substituted with up to three $R_{30}$;

$R_{11}$ at each occurrence is independently selected from halogen, cyano, $NO_2$, $C_{1-6}$alkyl, substituted $C_{1-6}$alkyl, $C_{2-6}$alkenyl, $C_{2-6}$alkynyl, haloalkyl, haloalkoxy, $-OR_{13}$, $-C(=O)R_{13}$, $-OC(=O)R_{13}$, $-CO_2R_{13}$, $-OCO_2R_{13}$, $-C(=O)NR_{13}R_{14}$, $-OC(=O)NR_{13}R_{14}$, $-NR_{13}R_{14}$, $-NR_{14}C(=O)R_{13a}$, $-NR_{14}CO_2R_{13}$, $-SR_{13}$, $-S(O)R_{13}$, $-SO_2R_{13}$, $-SO_2NR_{13}R_{14}$, $-SO_3R_{13}$, $-NR_{14}SO_2R_{13}$, and $-NR_{14a}SO_2NR_{13}R_{14}$; or alternatively, two $R_{11}$ groups may be taken together to form a fused benzo, heteroaryl, or heterocyclic ring, wherein said ring in turn is optionally substituted with up to one A group and/or one to two $R_{31}$; provided, however, that $R_{11}$ is not alkyl substituted with $-NR_{18a}C(=O)NR_{17}R_{18}$;

$R_{13}$, $R_{14}$, and $R_{14a}$ at each occurrence independently of each other are selected from hydrogen, $C_{1-6}$alkyl, substituted $C_{1-6}$alkyl, $C_{2-8}$alkenyl, $C_{2-8}$alkynyl, $C_{3-10}$cycloalkyl($C_{0-4}$alkyl), aryl($CO_{0-4}$alkyl), heterocyclo($C_{0-4}$alkyl), and heteroaryl($CO_{0-4}$alkyl), wherein each of said cycloalkyl, aryl, heterocyclo, and heteroaryl groups are optionally substituted with up to two substituents independently selected from $R_{32}$; provided, however, that when $R_{13}$ is attached to a sulfonyl group as in $-SO_2R_{13}$, $-S(=O)R_{13}$, and $-SO_3R_{13}$, then $R_{13}$ is not hydrogen; or alternatively, $R_{13}$ and $R_{14}$ can be taken together with the nitrogen atom to which they are attached to form a heterocyclo or heteroaryl, said ring being in turn optionally substituted with up to three groups selected from $R_{32}$;

$R_{13a}$ is selected from hydrogen, $C_{1-6}$alkyl, substituted $C_{1-6}$alkyl, $C_{2-8}$alkenyl, $C_{2-8}$alkynyl, $C_{3-10}$cycloalkyl($C_{0-4}$alkyl), aryl($C_{0-4}$alkyl), heterocyclo($C_{1-4}$alkyl), and heteroaryl($C_{1-4}$alkyl), wherein each of said cycloalkyl, aryl, heterocyclo, and heteroaryl groups are optionally substituted with up to two substituents independently selected from $R_{32}$;

$R_{15}$ at each occurrence independently of each other $R_{15}$ is selected from hydrogen, $C_{1-6}$alkyl, substituted $C_{1-6}$alkyl, $C_{2-8}$alkenyl, $C_{2-8}$alkynyl, $C_{3-10}$cycloalkyl($C_{0-4}$alkyl), aryl($C_{0-4}$alkyl), heterocyclo($C_{0-4}$alkyl), and heteroaryl($C_{0-4}$alkyl), wherein each of said cycloalkyl, aryl, heterocyclo, and heteroaryl groups are optionally substituted with up to two substituents independently selected from $R_{33}$; provided, however, that when $R_{15}$ is attached to a sulfonyl group as in $-SO_2R_{15}$, $-S(=O)R_{15}$, and $-SO_3R_{15}$, then $R_{15}$ is not hydrogen;

$R_{16}$ and $R_{16a}$ at each occurrence independently of each other $R_{16}$ and $R_{16a}$ are selected from hydrogen, $C_{1-6}$alkyl, substituted $C_{1-6}$alkyl, $C_{2-6}$alkenyl, $C_{2-6}$alkynyl, $-OR_{19}$, $-C(=O)R_{19}$, $-CO_2R_{19}$, $-SO_2R_{19}$, $C_{3-10}$cycloalkyl($C_{0-4}$alkyl), aryl($C_{0-4}$alkyl), heterocyclo($C_{0-4}$alkyl), and heteroaryl($C_{0-4}$alkyl), wherein $R_{19}$ is $C_{1-6}$alkyl, $C_{3-10}$cycloalkyl, aryl, heterocyclo, or heteroaryl, and each of said $R_{19}$, cycloalkyl, aryl, heterocyclo, and heteroaryl groups are in turn optionally substituted with up to two substituents independently selected from $R_{34}$;

alternatively, $R_{15}$ and $R_{16}$ can be taken together with the nitrogen atom to which they are attached to form a heterocyclo or heteroaryl, said ring being in turn optionally substituted with up to three groups selected from $R_{34}$;

$R_{17}$ and $R_{18}$ are independently selected from hydrogen, alkyl, substituted alkyl, cyano, hydroxy, alkoxy, cycloalkyl, heterocyclo, aryl and heteroaryl, or taken together may form a heteroaryl or heterocyclo ring;

$R_{17a}$ is hydrogen, alkyl, or substituted alkyl;

$R_{21}$, $R_{22}$, $R_{23}$, $R_{24}$, $R_{25}$, and $R_{26}$ are independently selected from halogen, cyano, hydroxy, $C_{1-3}$alkoxy, $OCF_3$, $CF_3$, amino, and $C_{1-6}$alkylamino;

$R_{27}$, $R_{28}$, $R_{29}$, $R_{30}$, $R_{31}$, $R_{32}$, $R_{33}$, and $R_{34}$ are at each occurrence independently selected from $C_{1-4}$alkyl, $C_{2-6}$alkenyl, $C_{2-6}$alkynyl, oxo (=O), halo($C_{0-4}$alkyl), $NO_2(C_{0-4}$alkyl), hydroxy($C_{0-4}$alkyl), $CF_3(C_{0-4}$alkyl), $OCF_3(C_{0-4}$alkyl), cyano($C_{0-4}$alkyl), amino($C_{0-4}$alkyl), $C_{1-4}$ alkoxy($C_{0-4}$alkyl), $C_{1-6}$alkylamino($C_{0-4}$alkyl), $C_{1-4}$ alkylthio($C_{0-4}$alkyl), carbamyl($C_{0-4}$alkyl), $-C(=O)C_{1-4}$ alkyl, $-CO_2C_{1-4}$ alkyl, $-S(O)(C_{1-4}$alkyl), $-SO_2(C_{1-4}$alkyl), $-SO_2NH_2$, $-SO_2NH(C_{1-4}$alkyl), $-SO_3H$, $-SO_3(C_{1-4}$alkyl), $-NHCO(C_{1-6}$alkyl), and $-C(=O)NH(C_{1-4}$alkyl), provided, however, that when $R_{26}$, $R_{27}$, $R_{30}$, $R_{31}$, $R_{32}$, $R_{33}$, and $R_{34}$ are substituents attached to an aryl or heteroaryl ring, said groups are not selected from oxo (=O); provided further, that when $R_{26}$, $R_{27}$, $R_{30}$, $R_{31}$, $R_{32}$, $R_{33}$, and $R_{34}$ are hydroxy and attached to an aryl or heteroaryl ring, the ring may undergo tautomerization to an oxo species, or exist as an equilibrium mixture of both tautomers;

a is 0 or 1;

m is 0, 1, or 2;

n is 0, 1, 2, 3, or 4;

p is 0, 1 or 2; and q is 0, 1, 2, 3 or 4.

Also included within the scope of the present invention are select compounds having surprisingly advantageous activity in inhibiting Factor VIIa.

DETAILED DESCRIPTION OF THE INVENTION

The following are definitions of terms used in this specification. The initial definition provided for a group or term herein applies to that group or term throughout this specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two, or three substituents selected from the group consisting of halogen, trifluoromethyl, trifluoromethoxy, alkenyl, alkynyl, nitro, cyano, keto (=O), —$OR_a$, —$SR_a$, —$NR_aR_b$, —$NR_aSO_2R_c$, —$SO_2R_c$, —$SO_2NR_aR_b$, —$CO_2R_a$, —C(=O)$R_a$, —C(=O)$NR_aR_b$, —OC(=O)$R_a$, —OC(=O)$NR_aR_b$, —$NR_aC$(=O)$R_b$, —$NR_aCO_2R_b$, cycloalkyl, heterocyclo, aryl, and heteroaryl, wherein $R_a$ and $R_b$ are independently selected from hydrogen, alkyl, alkenyl, cycloalkyl, heterocyclo, aryl, and heteroaryl, and $R_c$ is selected from alkyl, alkenyl, cycloalkyl, heterocyclo, aryl and heteroaryl. When a substituted alkyl (and/or $R_a$, $R_b$ and $R_c$) includes a cycloalkyl, heterocyclo, aryl, or heteroaryl substituent, said ringed systems are as defined below and thus may in turn have zero to three substituents (preferably 0–2 substituents), also as defined below. When $R_a$, $R_b$ or $R_c$ is an alkyl or alkenyl, said alkyl or alkenyl may optionally be substituted with 1–3 of halogen, trifluoromethyl, trifluoromethoxy, nitro, cyano, keto (=O), OH, —O(alkyl), phenyloxy, benzyloxy, SH, —S(alkyl), $NH_2$, —NH(alkyl), —N(alkyl)$_2$, —NHSO$_2$(alkyl), —SO$_2$(alkyl), —SO$_2$NH$_2$, —SO$_2$NH(alkyl), —SO$_2$N(alkyl)$_2$, —CO$_2$H, —CO$_2$(alkyl), —C(=O)H, —C(=O)alkyl, —C(=O)NH$_2$, —C(=O)NH(alkyl), —C(=O)N(alkyl)$_2$, —OC(=O)alkyl, —OC(=O)NH$_2$, —OC(=O)NH(alkyl), —NHC(=O)alkyl, and/or —NHCO$_2$(alkyl).

When the term "alkyl" is used in conjunction with another group such as in "arylalkyl" or "cycloalkylalkyl," such reference is intended to refer to a substituted alkyl in which at least one of the substituents is the specifically-named group, i.e., the group is bonded through an alkyl chain. For example, the term arylalkyl includes benzyl, or any other straight or branched chain substituted alkyl having at least one aryl group attached at any point of the alkyl chain. However, it should be understood that when the term "alkyl" is used following a bivalent linker preceeded by a bond designation, such as —C(=O)C$_{1-4}$alkyl, —S(O)C$_{1-4}$alkyl, —CO$_2$C$_{1-4}$alkyl, and —SO$_2$C$_{1-4}$alkyl, such references are intended to mean that the alkyl group is attached via the linker.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to three substitutents as defined above for alkyl groups. A substituted alkylene, alkenylene, or alkynylene may have a ringed substituent attached in a spiro fashion as in

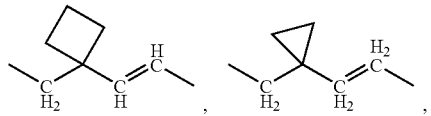

and so forth.

The term "alkoxy" refers to an alkyl, alkenyl, substituted alkyl, or substituted alkenyl group bonded through an oxygen atom (—O—). For example, the term "alkoxy" includes the groups —O—C$_{1-12}$alkyl, —O—C$_{2-8}$alkenyl, —S—CH$_2$aryl, and so forth.

The term "alkylthio" refers to an alkyl, alkenyl, substituted alkyl, or substituted alkenyl group bonded through a sulfur (—S—) atom. For example, the term "alkylthio" includes the groups —S—(CH$_2$)CH$_3$, —S—CH$_2$aryl, etc.

The term "alkylamino" refers to an alkyl, alkenyl, substituted alkyl or substituted alkenyl group bonded through a nitrogen (—NR'—) group. For example, the term "alkylamino" includes the groups —NR'—C$_{1-12}$alkyl and —NR'—CH$_2$-aryl, etc. (where R' is hydrogen, alkyl or substituted alkyl as defined above.) When a subscript is used with reference to an alkylamino group, the subscript refers to the total number of carbon atoms attached to the nitrogen atom. Thus, for example, C$_{1-6}$alkylamino includes groups such as —NHC$_{1-6}$alkyl, —N(C$_{1-3}$alkyl)$_2$, —N(C$_{1-2}$alkyl)(C$_{1-4}$alkyl), and so forth. "Amino" refers to the group —NH$_2$. The term "aminoalkyl" means a substituted alkyl having at least one amino substituent (e.g., C$_{1-2}$aminoalkyl includes —CH$_2$—NH$_2$, —CH$_2$—CH$_2$—NH$_2$, and —CH(NH$_2$)CH$_3$.) "Alkylaminoalkyl" means a substituted alkyl having at least one alkylamino substituent.

When a subscript is used as in C$_{1-8}$alkyl, the subscript refers to the number of carbon atoms the group may contain. Zero when used in a subscript denotes a bond, e.g., C$_{0-4}$alkyl refers to a bond or an alkyl of 1 to 4 carbon atoms. Thus, for example, "C$_{1-6}$alkyl" refers to straight and branched chain alkyl groups with one to six carbon atoms, such as methyl, ethyl, n-propyl, isopropyl, n-butyl, t-butyl, n-pentyl, and so forth. "Hydroxy(C$_{0-2}$alkyl)" includes hydroxy, hydroxymethyl, and hydroxyethyl. Similarly, "phenyl(C$_{0-2}$alkyl)" includes phenyl, phenylmethyl, and phenylethyl.

When used with alkoxy, thioalkyl, or alkylamino (or aminoalkyl), a subscript refers to the number of carbon atoms that the group may contain in addition to heteroatoms. Thus, for example, monovalent C$_{1-2}$alkylamino includes the groups —NH—CH$_3$, —NH—CH$_2$—CH$_3$, and —N(CH$_3$)$_2$. A lower alkylamino comprises an alkylamino having one to four carbon atoms.

The alkoxy, alkylthio, or alkylamino groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—$C_{1-2}$alkyl, whereas a bivalent alkoxy includes groups such as —O—$C_{1-2}$alkylene-, etc.

The term "acyl" refers to a group having a carbonyl

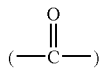

linked to an organic group i.e.,

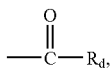

wherein $R_d$ may be selected from alkyl, alkenyl, substituted alkyl, substituted alkenyl, aryl, heterocyclo, cycloalkyl, and heteroaryl, as defined herein.

The term "alkoxycarbonyl" refers to a group having a carboxy or ester group

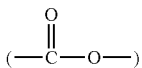

linked to an organic radical, i.e.,

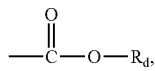

wherein $R_d$ is as defined above for acyl.

The term "carbamyl" refers to a functional group in which a nitrogen atom is directly bonded to a carbonyl, i.e., as in —$NR_eC(=O)R_f$ or —$C(=O)NR_eR_f$, wherein $R_e$ and $R_f$ can be hydrogen, alkyl, substituted alkyl, alkenyl, substituted alkenyl, alkoxy, cycloalkyl, aryl, heterocyclo, or heteroaryl, or when attached to the same nitrogen atom, $R_e$ and $R_f$ may join to form a ring.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "sulfonyl" refers to a sulphoxide group (i.e., —$S(O)_{1-2}$) linked to an organic radical $R_c$, as defined above.

The term "sulfonamidyl" or "sulfonamido" refers to the group —$S(O)_2NR_eR_f$, wherein $R_e$ and $R_f$ are as defined above in the definition for carbamyl. Preferably when one of $R_e$ and $R_f$ is optionally substituted heteroaryl or heterocyclo (as defined below), the other of $R_e$ and $R_f$ is hydrogen, alkyl, or substituted alkyl.

The term "cycloalkyl" refers to fully saturated and partially unsaturated hydrocarbon rings of 3 to 9, preferably 3 to 7 carbon atoms. The term "cycloalkyl" includes such rings having zero to three substituents (preferably 0–2 substituents), selected from 1) $R_g$; and 2) $C_{1-6}$ alkyl substituted with one to three $R_g$, wherein $R_g$ is selected from the group consisting of halogen, alkyl, alkenyl, substituted alkenyl, alkynyl, nitro, cyano, keto (=O), —$OR_a$, —$SR_a$, —$NR_aR_b$, —$NR_aSO_2R_c$, —$SO_2R_c$, —$SO_2NR_aR_b$, —$CO_2R_a$, —$C(=O)R_a$, —$C(=O)NR_aR_b$, —$OC(=O)R_a$, —$OC(=O)NR_aR_b$, —$NR_aC(=O)R_b$, —$NR_aCO_2R_b$, aryl, heteroaryl, heterocyclo, and/or another 4 to 7 membered cycloalkyl ring, wherein $R_a$, $R_b$ and $R_c$ are defined as above. When $R_a$, $R_b$ and $R_c$ are selected from an alkyl or alkenyl group, such groups are in turn optionally substituted as set forth above in the definition for substituted alkyl. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl has a second ring fused thereto or is substituted with a further ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two $C_{0-6}$alkyl substituted with one to two of (or bonded to one of) halogen, tirfluoromethyl, $C_{2-6}$alkenyl, nitro, cyano, keto (=O), OH, —O(alkyl), phenyloxy, benzyloxy, SH, —S(alkyl), $NH_2$, —NH(alkyl), —$N(alkyl)_2$, —$NHSO_2$(alkyl), —$SO_2$(alkyl), —$SO_2NH_2$, —$SO_2NH$(alkyl), —$SO_2N(alkyl)_2$, —$CO_2H$, —$CO_2$(alkyl), —C(=O)H, —C(=O)alkyl, —C(=O)$NH_2$, —C(=O)NH(alkyl), —C(=O)$N(alkyl)_2$, —OC(=O)alkyl, —OC(=O)$NH_2$, —OC(=O)NH(alkyl), —NHC(=O) alkyl, and —$NHCO_2$(alkyl).

Thus, the term "cycloalkyl" includes cyclopropyl, cyclobutyl, cyclopentyl, cyclohexyl, cycloheptyl, cyclooctyl, etc., as well as the following ring systems,

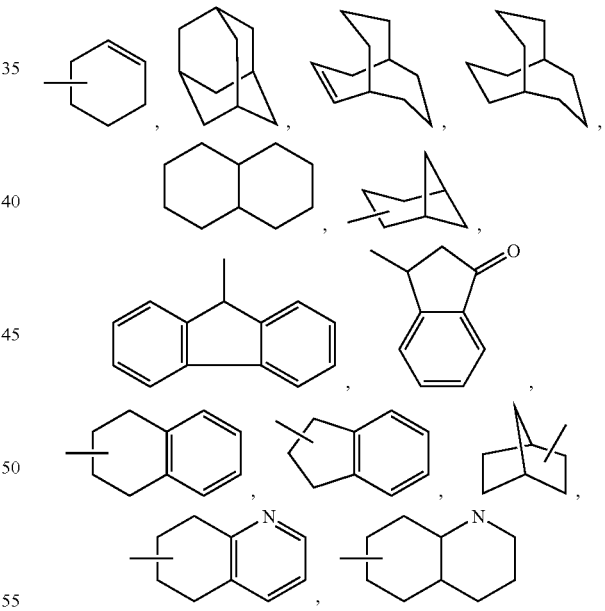

and the like, which optionally may be substituted at any available atoms of the ring(s).

The term "aryl" refers to phenyl, biphenyl, 1-naphthyl, and 2-naphthyl, with phenyl being preferred. The term "aryl" includes such rings having zero to three substituents (preferably 0–2 substituents), selected from the group consisting of 1) $R_h$; and 2) $C_{1-6}$ alkyl substituted with one to three $R_g$, wherein $R_g$ is as defined above for cycloalkyl, and $R_h$ is selected from the same groups as $R_g$ but does not include keto (=O). Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring, such ring in turn may be substituted with one to two $C_{0-6}$alkyl substituted with one to two of (or bonded to one of) halogen, tirfluoromethyl, $C_{2-6}$alkenyl, nitro, cyano, keto (═O), OH, —O(alkyl), phenyloxy, benzyloxy, SH, —S(alkyl), $NH_2$, —NH(alkyl), —N(alkyl)$_2$, —NHSO$_2$(alkyl), —SO$_2$(alkyl), —SO$_2$NH$_2$, —SO$_2$NH(alkyl), —SO$_2$N(alkyl)$_2$, —CO$_2$H, —CO$_2$(alkyl), —C(═O)H, —C(═O)alkyl, —C(═O)NH$_2$, —C(═O)NH(alkyl), —C(═O)N(alkyl)$_2$, —OC(═O)alkyl, —OC(═O)NH$_2$, —OC(═O)NH(alkyl), —NHC(═O)alkyl, and —NHCO$_2$(alkyl).

Thus, examples of aryl groups include:

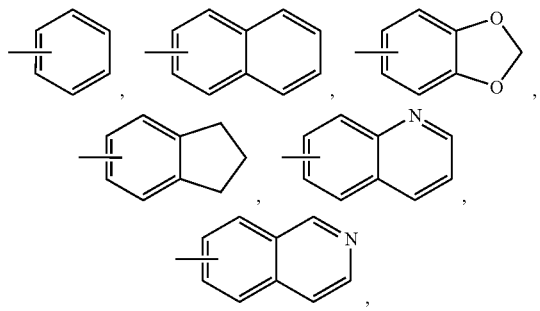

and the like, which optionally may be substituted at any available carbon or nitrogen atom.

The term "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclic ring may contain zero to three substituents (preferably 0–2 substituents), selected from 1) $R_g$; and 2) $C_{1-6}$ alkyl substituted with one to three $R_g$, wherein $R_g$ is defined as above for cycloalkyl groups. Additionally, when a heterocyclo is substituted with a further ring, such ring in turn may be substituted with one to two $C_{0-6}$alkyl substituted with one to two of (or bonded to one of) halogen, tirfluoromethyl, $C_{2-6}$alkenyl, nitro, cyano, keto (═O), OH, —O(alkyl), phenyloxy, benzyloxy, SH, —S(alkyl), $NH_2$, —NH(alkyl), —N(alkyl)$_2$, —NHSO$_2$(alkyl), —SO$_2$(alkyl), —SO$_2$NH$_2$, —SO$_2$NH(alkyl), —SO$_2$N(alkyl)$_2$, —CO$_2$H, —CO$_2$(alkyl), —C(═O)H, —C(═O)alkyl, —C(═O)NH$_2$, —C(═O)NH(alkyl), —C(═O)N(alkyl)$_2$, —OC(═O)alkyl, —OC(═O)NH$_2$, —OC(═O)NH(alkyl), —NHC(═O)alkyl, and —NHCO$_2$(alkyl).

Thus, exemplary heterocyclic groups include, without limitation:

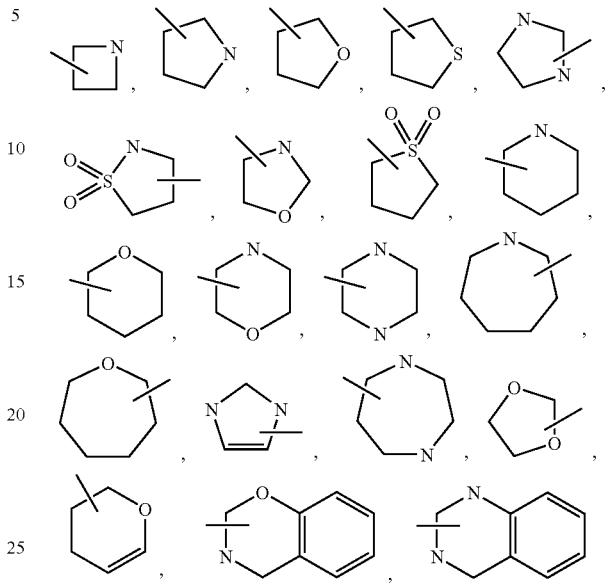

and the like, which optionally may be substituted at any available carbon or nitrogen atom.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to three substituents (preferably 0–2 substituents), selected from 1) $R_h$; and 2) $C_{1-6}$ alkyl substituted with one to three $R_g$, wherein $R_g$ and $R_h$ are defined above as for aryl groups. Additionally, when a heteroaryl is substituted with a further ring, such ring in turn may be substituted with one to two $C_{0-6}$alkyl substituted with one to two of (or bonded to one of) halogen, tirfluoromethyl, $C_{2-6}$alkenyl, nitro, cyano, keto (═O), OH, —O(alkyl), phenyloxy, benzyloxy, SH, —S(alkyl), $NH_2$, —NH(alkyl), —N(alkyl)$_2$, —NHSO$_2$(alkyl), —SO$_2$(alkyl), —SO$_2$NH$_2$, —SO$_2$NH(alkyl), —SO$_2$N(alkyl)$_2$, —CO$_2$H, —CO$_2$(alkyl), —C(═O)H, —C(═O)alkyl, —C(═O)NH$_2$, —C(═O)NH(alkyl), —C(═O)N(alkyl)$_2$, —OC(═O)alkyl, —OC(═O)NH$_2$, —OC(═O)NH(alkyl), —NHC(═O)alkyl, and —NHCO$_2$(alkyl).

Examples of heteroaryl rings include

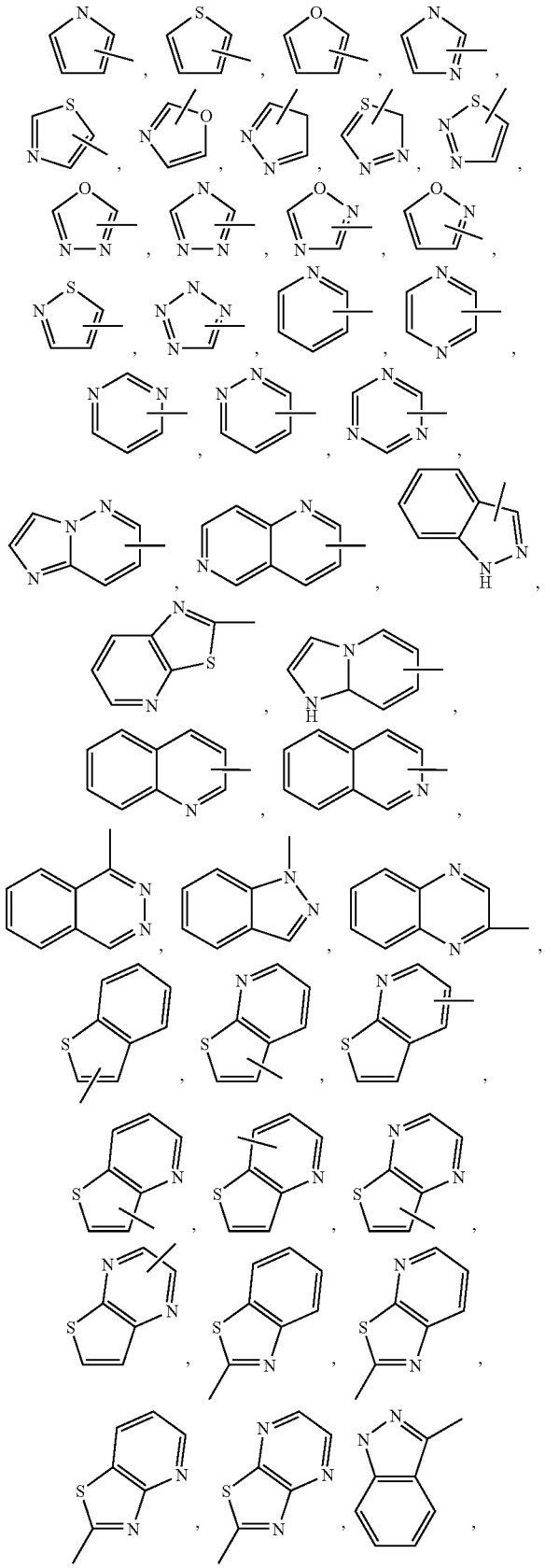

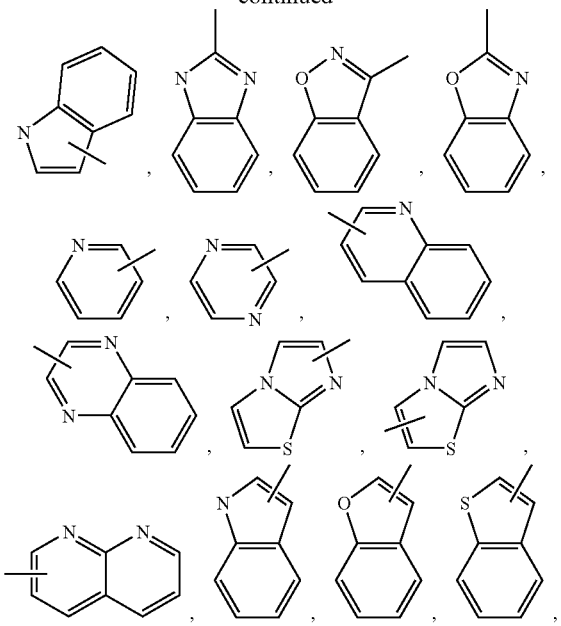

and the like, which optionally may be substituted at any available carbon or nitrogen atom.

The term "carbocyclic" refers to optionally substituted aromatic or non-aromatic 3 to 7 membered monocyclic and 7 to 11 membered bicyclic groups, in which all atoms of the ring or rings are carbon atoms. A carbocyclic ring system may optionally be substituted as defined above for aryl and cycloalkyl groups.

When the term "unsaturated" is used herein to refer to a ring or group, the ring or group may be fully unsaturated or partially unsaturated.

When reference is made to a specifically -named ringed group, such as cyclohexyl, phenyl, morpholinyl, oxazolyl, and the like, it should be understood that, unless the presence or absence of substituents is otherwise specifically stated, these groups optionally may be substituted as recited above for the corresponding genus of rings in which they belong.

When reference is made generally to a monocyclic or bicyclic ring system, such reference is intended to include cycloalkyl, aryl, heterocyclo, and heteroaryl rings, as defined above.

The term "metal ion" refers to alkali metal ions such as sodium, potassium or lithium and alkaline earth metal ions such as magnesium and calcium, as well as zinc and aluminum.

Whenever a bond appears in a formula as a dashed-double bond, i.e., with one bond appearing as a dash as in

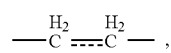

it should be understood that such bonds may be selected from single or double bonds, as appropriate given the selections for adjacent atoms and bonds.

Multiple substituents may be selected for any compound within the scope of this invention; however, advantageously substituents are selected so that the compounds of formula (I) have a molecular weight of less than 1,500. More preferred are compounds having a molecular weight of less than 1,000, and even more preferred are compounds having a molecular of less than 500.

It should be understood that one skilled in the field may make various substitutions for each of the groups recited in the claims herein, without departing from the spirit or scope of the invention.

Throughout the specification, groups and substituents thereof may be chosen by one skilled in the field to provide stable moieties and compounds.

The compounds of the present invention form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of the present invention contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the present invention may be formed, for example, by reacting a compound of the present invention with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the present invention, and/or a salt and/or solvate thereof. Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, 113–191 (1991); and c) H. Bundgaard, *Advanced Drug Delivery Reviews*, 8, 1–38 (1992), each of which is incorporated herein by reference.

Compounds containing a carboxy group can form physiologically hydrolyzable esters which serve as prodrugs by being hydrolyzed in the body to yield the present invention compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the present invention or salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

The compounds of the instant invention may, for example, be in the free or hydrate form, and may be obtained by methods exemplified by the following descriptions.

Preferred Compounds

The methods of the invention preferably comprise administration of compounds of formula (I),

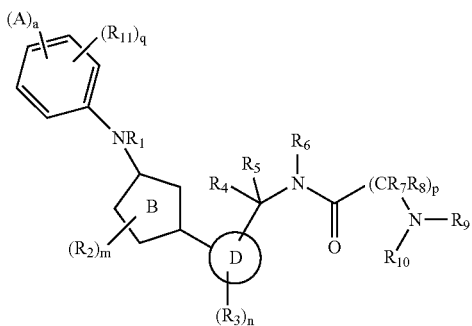

or pharmaceutically-acceptable salts, hydrates, and prodrugs thereof, in which:

A is selected from phenyl, oxazolyl, thiazolyl, isothiazolyl, imidazolyl, furyl, thienyl, thiadiazolyl, oxadiazolyl, tetrazolyl, triazolyl, diazoly, pyrrolyl, and pyrazolyl, said ring A being optionally substituted with up to two groups selected from halogen, $C_{1-4}$alkyl, haloalkyl, haloalkoxy, OH, $C_{1-4}$alkoxy, $C_{1-4}$alkylcarbonyl, CN, $NH_2$, $NH(C_{1-4}$alkyl), and $N(alkyl)_2$;

B is

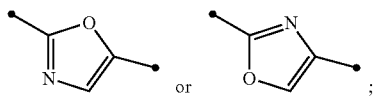

D is phenyl, or A is a carbocyclic ring and D is selected from pyridyl, pyrazinyl, pyrimidinyl, pyridazinyl, furanyl, thiophenyl, and pyrrolyl;

$R_1$ is selected from hydrogen, $C_{1-4}$alkyl, and $C_{1-4}$alkyl substituted with one of halogen, hydroxy, amino, $C_{1-3}$alkoxy, or $C_{1-6}$alkylamino;

$R_2$ and $R_3$ are attached to any available carbon atom of ring B and ring D, respectively, and at each occurrence are independently selected from halogen, cyano, $C_{1-4}$alkyl, hydroxy($C_{0-4}$alkyl), $CF_3(C_{0-4}$alkyl), $OCF_3(C_{0-4}$alkyl), cyano($C_{1-4}$alkyl), amino($C_{0-4}$alkyl), $C_{1-4}$alkoxy($C_{0-4}$alkyl), $C_{1-6}$alkylamino($C_{0-4}$alkyl), and $C_{1-4}$alkylthio($C_{0-4}$alkyl);

$R_4$, $R_5$, $R_6$, $R_7$ and $R_8$ are independently selected from hydrogen and $C_{1-4}$alkyl;

$R_9$ and $R_{10}$ are independently selected from hydrogen, $C_{1-4}$alkyl, and $C_{1-4}$alkyl substituted with one to two $R_{25}$; or alternatively, $R_9$ and $R_{10}$ taken together may form a 3–8 membered heterocyclic ring or a five to six membered heteroaryl ring, said ring being optionally substituted with up to three $R_{30}$;

$R_{11}$ at each occurrence is independently selected from halogen, cyano, $C_{1-4}$alkyl, hydroxy($C_{0-4}$alkyl), $CF_3(C_{0-4}$alkyl), $OCF_3(C_{0-4}$alkyl), cyano($C_{1-4}$alkyl), amino($C_{0-4}$alkyl), $C_{1-4}$alkoxy($C_{0-4}$alkyl), $C_{1-6}$alkylamino($C_{0-4}$alkyl), and $C_{1-4}$alkylthio($C_{0-4}$alkyl), or two $R_{11}$ groups may be taken together to form a fused benzo, heteroaryl, or heterocyclic ring, wherein said ring in turn is optionally substituted with up to one A group and/or one to two of hydrogen, halogen, $C_{1-4}$alkyl, hydroxy($C_{0-4}$alkyl), $CF_3(C_{0-4}$alkyl), $OCF_3(C_{0-4}$alkyl), cyano($C_{0-4}$alkyl), and $C_{1-4}$alkoxy($C_{0-4}$alkyl);

$R_{25}$ is halogen, hydroxy, $C_{1-3}$alkoxy, amino, or $C_{1-6}$alkylamino;

$R_{30}$ is selected from $C_{1-4}$alkyl, oxo (=O), halo($C_{0-4}$alkyl), hydroxy($C_{0-4}$alkyl), $CF_3(C_{0-4}$alkyl), $OCF_3(C_{0-4}$alkyl), cyano($C_{0-4}$alkyl), amino($C_{0-4}$alkyl), $C_{1-4}$alkoxy($C_{0-4}$alkyl), $C_{1-6}$alkylamino($C_{0-4}$alkyl), $C_{1-4}$alkylthio($C_{0-4}$alkyl), —C(=O)$C_{1-4}$alkyl, and —$CO_2C_{1-4}$alkyl;

a is 0 or 1;
m is 0, 1, or 2;
n is 0, 1, 2, 3, or 4;
p is 0, 1 or 2; and
q is 0, 1, 2, 3 or 4.

The methods of the invention preferably comprise administration of compounds of formula (I), where A is selected from phenyl, oxazolyl, thiazolyl, isothiazolyl, imidazolyl, furyl, thienyl, thiadiazolyl, oxadiazolyl, tetrazolyl, triazolyl, diazolyl, pyrrolyl, and pyrazolyl, said ring A being optionally substituted with up to two groups selected from halogen, $C_{1-4}$alkyl, trifluoromethyl, or cyano. More preferably A is oxazolyl which is unsubstituted or substituted with $C_{1-2}$alkyl, and D is carbocyclic.

The methods of the invention preferably comprise administration of compounds of formula (I), where B is

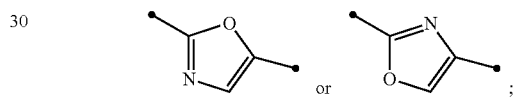

more preferably B is

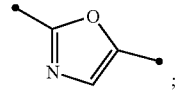

and even more preferred are compounds where B is

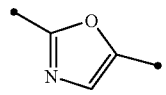

and is unsubstituted. Thus, $R_2$ is preferably absent (or $R_{2a}$ is preferably hydrogen).

The methods of the invention preferably comprise administration of compounds of formula (I), where D is selected from phenyl, pyridyl, pyrazinyl, pyrimidinyl, pyridazinyl, furanyl, thiophenyl, and pyrrolyl; more preferred are compounds where D is phenyl.

The methods of the invention preferably comprise administration of compounds of formula (I), where $R_3$ is absent, or is attached to any available carbon atom of ring D and at each occurrence is independently selected from halogen, cyano, $C_{1-4}$alkyl, hydroxy($C_{0-4}$alkyl), $CF_3(C_{0-4}$alkyl), $OCF_3$ ($C_{0-4}$alkyl), cyano($C_{1-4}$alkyl), amino($C_{0-4}$alkyl), $C_{1-4}$alkoxy ($C_{0-4}$alkyl), $C_{1-6}$alkylamino($C_{0-4}$alkyl), and $C_{1-4}$alkylthio ($C_{0-4}$alkyl). More preferred are methods comprising use of compounds where $R_3$ is absent or if present, is halogen, more preferably fluoro, wherein n is 1–4.

In the methods of the invention, preferably $R_6$ is selected from $C_{1-4}$alkyl; more preferably methyl.

The methods of the invention preferably comprise administration of compounds of formula (I), where $R_4$, $R_5$, $R_7$, $R_8$, $R_9$ and $R_{10}$ are each selected from hydrogen and $C_{1-4}$alkyl; more preferably each of said groups is hydrogen.

The methods of the invention preferably comprise administration of compounds of formula (I), where $R_{11}$ is selected from halogen, cyano, $C_{1-4}$alkyl, $CF_3$, $OCF_3$ and $C_{1-4}$alkoxy, and q is 0 or 1.

Also preferred in practicing the methods of the invention are compounds having the formula (Ia),

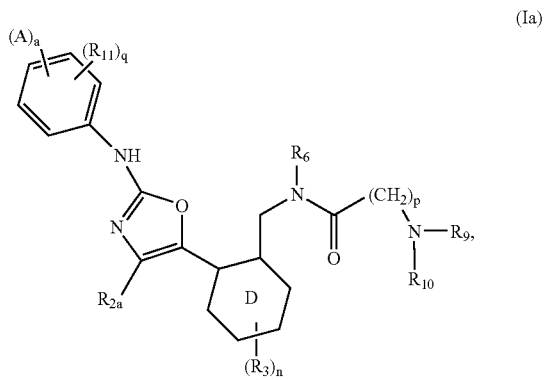

(Ia)

or pharmaceutically-acceptable salts, hydrates, or prodrugs thereof, in which:

A is selected from phenyl, oxazolyl, thiazolyl, isothiazolyl, imidazolyl, furyl, thienyl, thiadiazolyl, oxadiazolyl, tetrazolyl, triazolyl, diazolyl, pyrrolyl, and pyrazolyl, said ring A being optionally substituted with up to two groups selected from halogen, $NO_2$, $C_{1-4}$alkyl, haloalkyl, haloalkoxy, OH, $C_{1-4}$alkoxy, $C_{1-4}$alkylcarbonyl, CN, $NH_2$, $NH(C_{1-4}$alkyl), and $N(alkyl)_2$;

D is phenyl, or when A is phenyl, then D is selected from pyridyl, pyrazinyl, pyrimidinyl, pyridazinyl, furanyl, thiophenyl, and pyrrolyl;

$R_{2a}$ is selected from hydrogen, halogen, and $C_{1-4}$alkyl;

$R_3$ is selected from halogen, $C_{1-4}$alkyl, $CF_3$, $OCF_3$, cyano, and $C_{1-3}$alkoxy;

$R_6$ is $C_{1-4}$alkyl;

$R_{11}$, is selected from hydrogen, halogen, $C_{1-4}$alkyl, hydroxy($C_{0-4}$alkyl), $CF_3(C_{0-4}$alkyl), $OCF_3(C_{0-4}$alkyl), cyano($C_{0-4}$alkyl), amino($C_{0-4}$alkyl), $C_{1-3}$alkoxy($C_{0-4}$alkyl), and $C_{1-6}$alkylamino($C_{0-4}$alkyl), or two $R_{11}$ groups may be taken together to form a fused benzo, heteroaryl, or heterocyclic ring, wherein said ring in turn is optionally substituted with up to one A group and/or one to two of hydrogen, halogen, $C_{1-4}$alkyl, hydroxy($C_{0-4}$alkyl), $CF_3(C_{0-4}$alkyl), $OCF_3(C_{0-4}$alkyl), cyano($C_{0-4}$alkyl), and $C_{1-4}$alkoxy($C_{0-4}$alkyl);

$R_9$ and $R_{10}$ are independently selected from hydrogen and $C_{1-4}$alkyl;

a is 0 or 1;

n is 0, 1, 2, 3, or 4;

p is 0, 1 or 2; and q is 0, 1, or 2.

Most preferred are the inventive methods comprising administration of the compounds as immediately defined above, wherein A is oxazolyl that is unsubstituted or substituted with $C_{1-2}$alkyl; D is phenyl; $R_{2a}$ is hydrogen; $R_3$ is absent (n is 0), or $R_3$ is halogen, more preferably fluoro (and n is 1–4); $R_6$ is methyl; $R_{11}$ is hydrogen, halogen, or methoxy; $R_9$ and $R_{10}$ are hydrogen; a is 0 or 1; and p is 1.

The invention also relates to preferred compounds of the present invention, exemplified herein and as defined above, which have demonstrated activity in inhibiting Factor VIIa with $IC_{50}$ values (concentration required to inhibit 50% of specific binding) below 1 µM, and more preferred compounds that have demonstrated $IC_{50}$ values of below 500 nM.

Methods of Preparation

The compounds of the present invention may be synthesized using conventional techniques known in the art. Advantageously, these compounds are conveniently synthesized from readily-available starting materials. Additionally, illustrative general synthetic schemes for making compounds of the present invention are set forth below, and methods for making the compounds useful to the invention are also set forth in the Examples that follow hereinafter. In these schemes, the group Q may designate the substituent $R_{11}$ or an appropriate precursor thereto, which one skilled in the field may select as appropriate for a given reaction. Groups designated A, D, etc., are also intended to refer to such groups as recited in the claims.

The preparation of heterocycles useful to this invention is described in the literature, e.g., Katritzky et al., "Comprehensive Heterocyclic Chemistry, The Structure, Reactions, Synthesis and Uses of Heterocyclic Compounds," (Pergamon Press New York, 1984 [1st Ed.], and 1996). Methods of preparation useful to make compounds of this invention also may be described in U.S. Pat. No. 6,399,773, which is incorporated herein by reference.

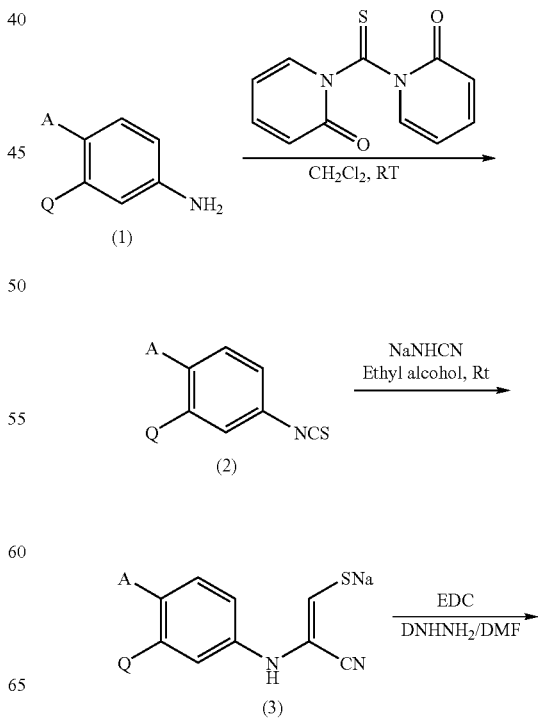

Scheme 1

-continued

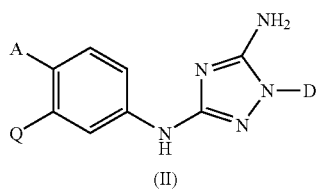
(II)

Reaction of an appropriately-substituted amine (1) with a reagent such as 1,1'-thiocarbonyldi-2(1H)-pyridone, 1,1'-thiocarbonyldiimidazole or thiophosgene in a solvent such as methylene chloride or dioxane yields the isothiocyanate (2). Treatment of the isothiocyanate (2) with sodium salt of cyanamide yields the sodium salt of N-cyanothiourea (3), which is cyclized to the substituted 1,2,4-aminotriazole (II), using an appropriately-substituted hydrazine and a dehydrating agent such as EDC or DCC.

Scheme 2

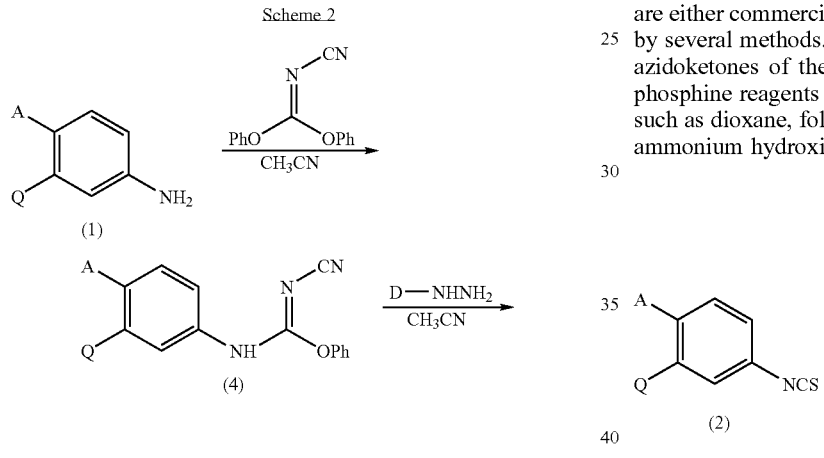

An appropriately-substituted amine (1) can be reacted with diphenyl cyanocarbonimidate to yield the N-cyano-O-phenylisourea (4). Cyclization of compound (4) to the substituted triazole (II) is achieved using an appropriately-substituted hydrazine and a solvent such as acetonitrile.

Scheme 3

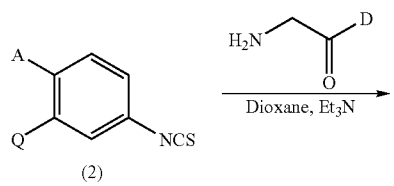

-continued

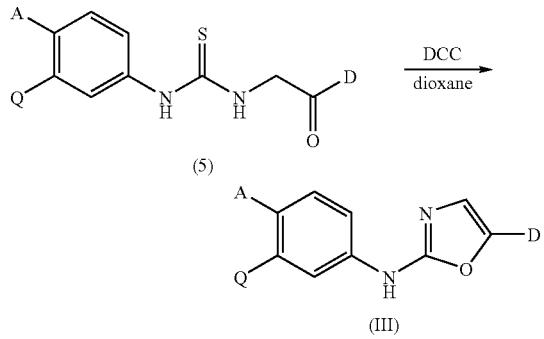

Reaction of an isothiocyanate (2) with a β-ketoamine in the presence of a base such as TEA and a solvent such as dioxane yields the thiourea (5). Reaction of the thiourea in the presence of a dehydrating agent such as dicyclohexylcarbodiimide or EDC, in a solvent such as dioxane or toluene, at a temperature preferably between 60° C. and 110° C., yields the desired 2-aminooxazoles (III). β-ketoamines are either commercially available or can be readily prepared by several methods. One exemplary method is reduction of azidoketones of the type described in schemes 5a–5d, by phosphine reagents such as triphenylphosphine in a solvent such as dioxane, followed by the addition of water or dilute ammonium hydroxide.

Scheme 4

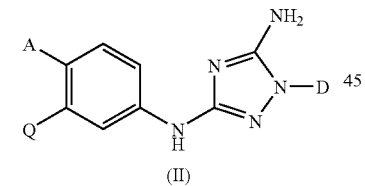

Reaction of an appropriately-substituted isothiocyanate (2) with an acylazide of the type described in schemes 5a–5b in the presence of a phosphine such as triphenyphosphine in a solvent such as DCM or dioxane at a temperature from rt to 100° C., also yields compounds (III). One skilled in the field will recognize that caution should be exercised while handling organic azides.

Scheme 5a

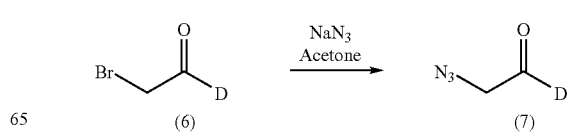

Treatment of the α-bromoketone (6) with sodium azide in a solvent such as acetone, generally at rt, yields the desired α-azidoketones (7) useful as intermediates in this invention. α-Bromoketones (6) are commercially available. Alternatively, α-bromoketones can be readily prepared from a ketone [CH₃—C(=O)D], by (a) reaction with a brominating agent such as bromine in acetic acid or pyridinium bromide perbromide and 30% hydrobromic acid; (b) reaction with a carboxylic acid, iso-butylchloroformate and N-methylmorpholine to provide the mixed anhydride, which on treatment with diazomethane (CH₂N₂) gives the α-diazoketone. Reaction of the α-diazoketone with either HBr gas in a solvent such as ether or dioxane, or aqueous 48% HBr, provides the α-bromoketone (6); or (c) reaction with sulfuric acid and bromine which yields the α,α-dibromoketone, which on treatment with diethylphosphite and TEA yields the α-(mono)bromoketone (6).

Scheme 5b

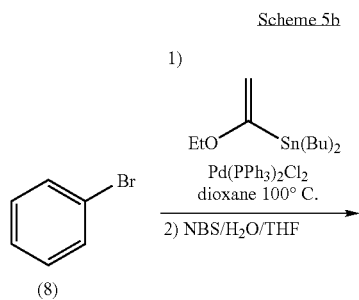

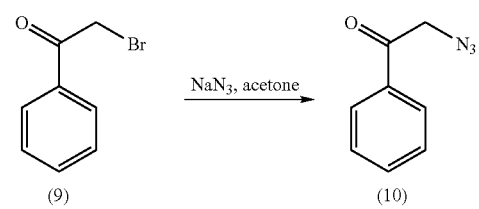

Reaction of an aryl bromide (8) with tributyl(1-ethoxyvinyl) tin and bis-(triphenylphosphine)palladium dichloride provides an intermediate enol ether. Treatment of the enol ether with N-bromosuccinamide at a temperature from 0° C. to rt yields the α-bromoketone (9). As described in Scheme 5a, treatment of the αbromoketone with sodium azide in acetone gives the α-azidoketone (10).

Scheme 6

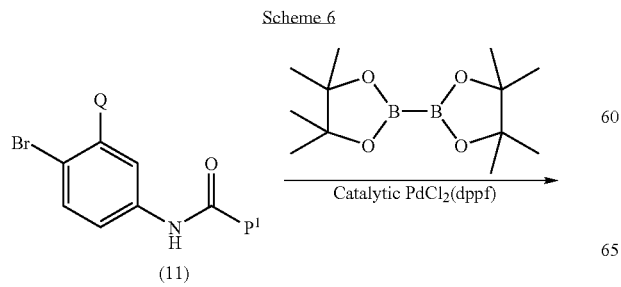

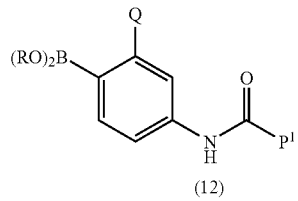

Aryl boronic acids and esters of type (12), may be prepared from the corresponding arylbromide (11) by treatment with a palladium catalyst such as [1,1'-Bis(diphenylphosphino)-ferrocene] dichloropalladium (II) and bis(pinacolato)diboron, as reported by Ishayama et al., *J. Org. Chem.*, 1995, 7508–7510. Aryl boronic esters may be converted to the corresponding boronic acids by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of CaCl₂ in a solvent such as EtOH, or in certain cases the nitro group may be reduced by catalytic hydrogenation in the presence of catalysts such as Pd/C. The conditions for the reduction of nitro groups are detailed in several references including Hudlicky, M., "Reductions in Organic Chemistry", 2nd Ed., ACS Monograph 188 (1996), pp. 91–101. In a second variation of the synthesis, the aryl bromide is allowed to remain through the entire synthesis and elaborated to the boronic acid at the end. This may eliminate the need for a protecting group.

Scheme 8

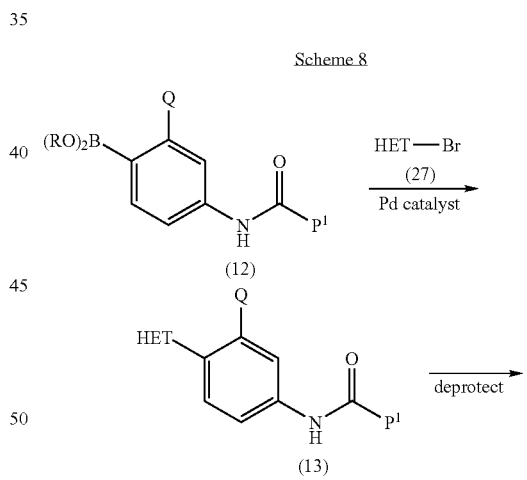

Suzuki-type cross coupling of an aryl boronic acid or ester (12) with an appropriate bromoheterocycle (13) in the presence of a suitable catalyst such as Pd(PPh₃)₄ yields the desired protected amide (14) (see, e.g., Miyaura et al., *Synth. Comm.*, 1981, 11(7), 513–19; Suzuki et al., *J. Am. Chem. Soc.* 1989, 111:513; and Kalinin, *Russ. Chem. Rev.*, 1991, 60, 173). The amide (13) may be deprotected as known to one skilled in the art (see, e.g., Greene and Wuts, *Protective Groups in Organic Synthesis*, (John Wiley and Sons, Inc., New York, N.Y. 1991). For example, if the protecting group is acetyl, the product may be deprotected by treatment with aqueous KOH at a concentration of 0.5 N to 5 N at rt to 100° C for a period between 0.5 h and 24 h, to provide amine (14), an intermediate for making compounds according to the invention. Compounds (12) can be prepared as shown in Scheme 6.

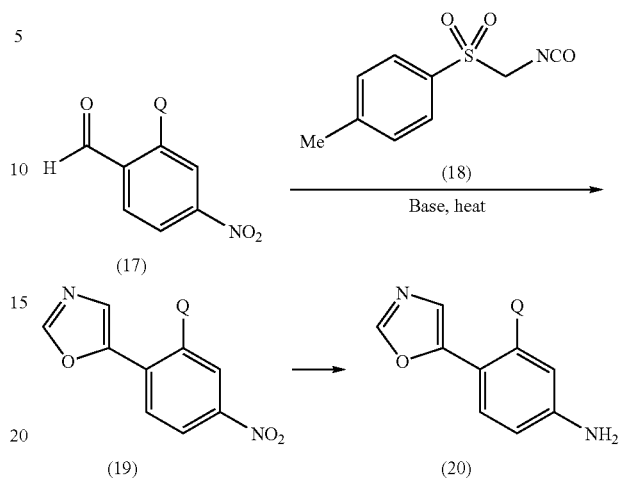

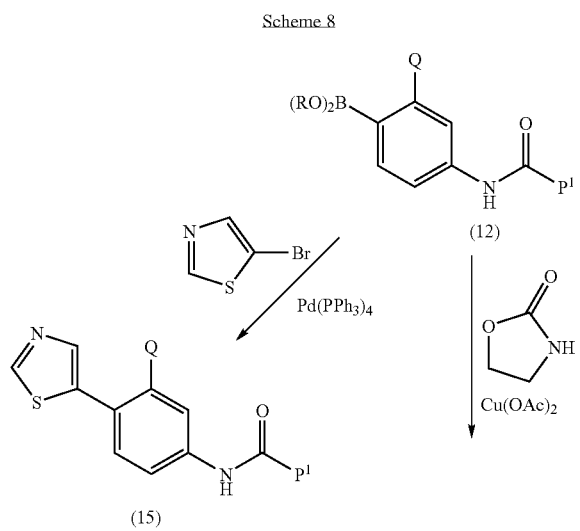

Oxazoles may be prepared by 1,3 dipolar cycloaddition of the corresponding aldehyde (17) and (p-tolylsulfonyl)methyl isocyanate (TOSMIC) (19). The aldehyde may be commercially available or prepared from the corresponding methyl group by oxidation with reagents such as $CrO_3$, $MnO_2$, and ammonium cerium (IV) nitrate. These methods are well known to one skilled in the art and described in Hudlicky, M., *Oxidations in Organic Chemistry*, ACS Monograph 186 (1990). The nitro group in intermediate (19) is reduced to an amine (20) by methods known in the field. Synthesis of 5-membered heterocycles by 1,3-dipolar cycloaddition is also described by Padwa, *1,3-Dipolar Cycloaddition Chemistry*, Vols. 1 & 2 (John Wiley and Sons, New York, N.Y., 1984).

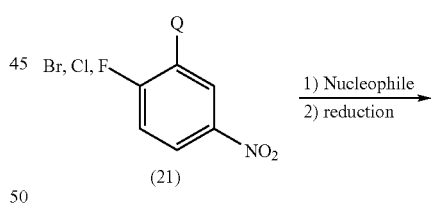

Aryl boronic acid (12) may be reacted with 5-bromothiazole in the presence of $Pd(PPh_3)_4$, to provide (15). Alternatively, aryl boronic acid (12) may be reacted with oxazolone in the presence of copper (II) acetate and an amine base such as pyridine to provide intermediate (16). Compounds (15) and (16) may be deprotected by an appropriate method. Copper has been shown to be an effective catalyst for cross coupling of aryl boronic acids to N-unsubstituted heterocycles as described by Chan. et al., *Tetrahed. Lett.*, 1998, 39, 2933–36; and Lam et al., *Tetrahed. Lett.*, 1998, 39,2941 – 44. This results in compounds in which the heterocycle is attached to the aryl ring through nitrogen rather than carbon.

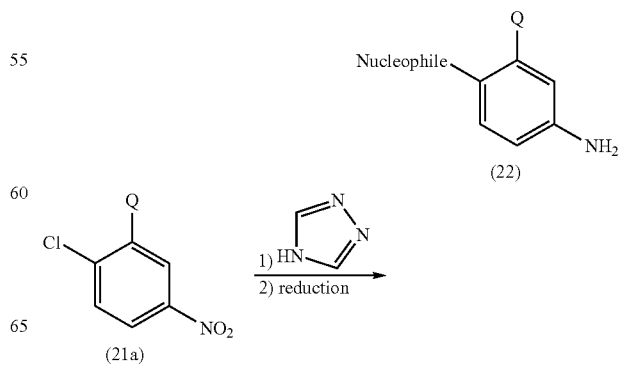

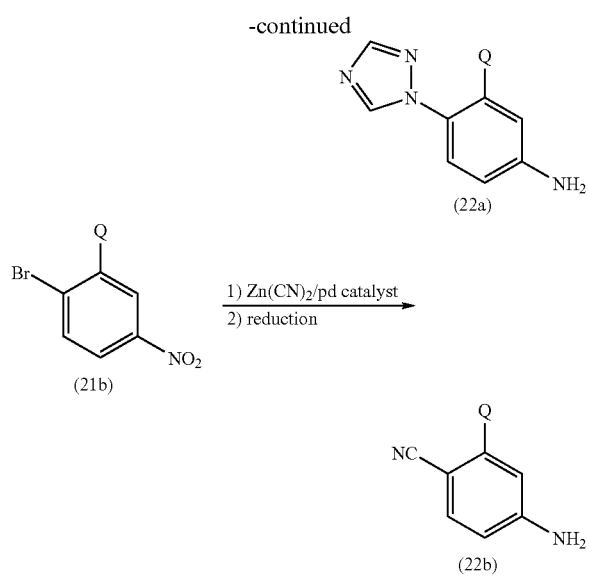

Halonitrobenzenes (21) are either commercially available or can be readily prepared by methods known to one skilled in the art. Displacement of halonitrobenzenes (21) with a variety of nucleophiles produces compounds of structure (22). In one example, heating (21 a) with a nucleophilic heterocycle such as triazole with or without the addition of a base provides the intermediate nitro compound which may be reduced as previously described to provide amines (22a). Alternatively, simple organic nucleophiles such as cyanide can be reacted with halonitrobenzene (21b) to provide an intermediate nitrocompound which can be reduced by many methods to produce amine (22b).

Utility

The inventive compounds are inhibitors of the serine protease FVIIa. Thus, the compounds are useful for treating or preventing those processes, which involve the action of Factor VIIa. As used herein with reference to the utilities described below, the term "treating" or "treatment" encompasses either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their above-referenced FVIIa inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

In addition, the inventive compounds are useful in preventing venous thrombosis, coagulation syndromes, deep vein thrombosis (DVT), disseminated intravascular coagulopathy, Kasabach-Merritt syndrome, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In addition, the compounds of the present invention may be useful in treating cancer and preventing the prothrombotic complications of cancer. The compounds may be useful in treating tumor growth, as an adjunct to chemotherapy, for preventing angiogenesis, and for treating cancer, more particularly, cancer of the lung, prostate, colon, breast, ovaries, and bone.

The inventive compounds may also be used in combination with other antithrombotic or anticoagulant drugs such as thrombin inhibitors, platelet aggregation inhibitors such as aspirin, clopidogrel, ticlopidine or CS-747, warfarin, low molecular weight heparins (such as LOVENOX), GPIIb/GPIIIa blockers, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, itavastatin (Nissan/Kowa), and compounds disclosed in U.S. provisional applications No. 60/211,594 filed Jun. 15, 2000, and No. 60/211,595 filed Jun. 15, 2000; microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel and the like. The inventive compounds are also useful in combination with anti-arrhythmic agents such as for atrial fibrillation, for example, amiodarone or dofetilide.

The inventive compounds may be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive compounds may also be used in combination with β-adrenergic agonists such as albuterol, terbutaline, formoterol, salmeterol, bitolterol, pilbuterol, or fenoterol; anticholinergics such as ipratropium bromide; anti-inflammatory corticosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

The inventive compounds may also be useful in combination with other anticancer strategies and chemotherapies such as taxol and/or cisplatin.

The compounds may act synergistically with one or more of the above agents. For example, the inventive compounds may act synergistically with the above agents to prevent reocclusion following a successful thrombolytic therapy and/or reduce the time to reperfusion. Thus, reduced doses of thrombolytic agent(s) may be used, therefore minimizing potential hemorrhagic side effects.

The compounds of the present invention may be administered by any means suitable for the condition to be treated, which may depend on the need for site-specific treatment or quantity of drug to be delivered. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories, or in the form of liposome particles. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of the present invention may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

Factor VIIa Assay

Compound was prepared as a 5 mM stock in DMSO, diluted further in DMSO and added directly to the assays. The DMSO concentration for all these studies was less than 1% and compared to DMSO vehicle controls.

Human Factor VIIa was obtained from Enzyme Research Labs (Cat.# HFVIIA 1640). Human recombinant tissue factor (INNOVIN from Dade Behring Cat.# B4212-100; "20 ml vial") was diluted with 8 ml of $H_2O$ per vial and diluted further 1:30 into the 302 µl final assay volume. Tissue factor activated FVIIa enzymatic activity was measured in a buffer containing 150 mM NaCl, 5 mM $CaCl_2$, 1 mM CHAPS and 1 mg/ml PEG 6000 (pH 7.4) with 1 nM FVIIa and 100 µM D-Ile-Pro-Arg-AFC (Enzyme Systems Products, Km>200 µM) 0.66% DMSO. The assay (302 µl total volume) was incubated at RT for 2 hr prior to reading fluorometric signal (Ex 405/Em 535) using a Victor 2 (Wallac) fluorescent plate reader.

To determine the compound concentration that inhibited half of the enzyme activity ($IC_{50}$), the fraction of control activity (FCA) was plotted as a function of the inhibitor concentration and curve to fit $FCA/(1[I]/IC_{50})$. The $IC_{50}$ for each compound was determined 2–4 times and the obtained values were averaged.

Applying the above-described assays, the inventive compounds demonstrated activity as inhibitors of Factors VIIa.

The following Examples illustrate embodiments of the inventive compounds and starting materials, and are not intended to limit the scope of the claims. For ease of reference, the following abbreviations are used herein:

Abbreviations
Me=methyl
Et=ethyl
Ph=phenyl
Bn=benzyl
t-Bu=tertiary butyl
Boc=tert-butoxycarbonyl
CBZ=carbobenzyloxy or carbobenzoxy or benzyloxycarbonyl
THF=tetrahydrofuran
EtOAc=ethyl acetate
DMF=dimethyl formamide
i-PrOH=isopropanol
DMSO=dimethyl sulfoxide
DME=1,2 dimethoxyethane
DCE=1,2 dichloroethane
DCM=dichloromethane
AcOH=acetic acid
TFA=trifluoroacetic acid
i-Pr$_2$NEt=diisopropylethylamine
DMAP=4-dimethylaminopyridine
NMM=N-methyl morpholine
$NaHCO_3$=sodium bicarbonate
$NaBH(OAc)_3$=sodium triacetoxyborohydride
Pd/C=palladium on carbon
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
Pd(OAc)$_2$=Palladium acetate
CBZ-Cl=benzyl chloroformate
SAX=Strong Anion Exchanger
SCX=Strong Cation Exchanger
PVP=polyvinylpyridine
DCC=dicyclohexylcarbodiimide
DIC or DIPCDI=diisopropylcarbodiimide
DMA=dimethyl acetamide
DIAD=diisopropyl azodicarboxylate
DIEA=diisopropylethylamine
DIPEA=diisopropylethylamine
DPPF=1,1'-bis(diphenylphosphino)ferrocene
TEA=triethylamine
TBS=t-butyldimethylsilyl
Tf=trifluoromethanesulfonyl
L=liter
mL=milliliter
µL=microliter
g=gram(s)
h=hour(s)
mg=milligram(s)
meq=milliequivalent
min=minute(s)
rt or RT=room temperature
conc.=concentrated
sat or sat'd=saturated
TLC=thin layer chromatography
HPLC=high performance liquid chromatography
RP HPLC=reverse phase HPLC
LC/MS=high performance liquid chromatography/mass spectrometry
MS or Mass Spec=mass spectrometry
MW=molecular weight
mp =melting point

EXAMPLE 1

2-Amino-N-{2-[2-(3-methoxy-4-oxazol-5-yl-phenylamino)-oxazol-5-yl]-benzyl}-N-methyl-acetamide

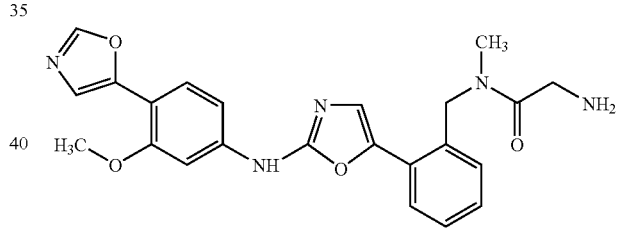

Part A. (2-Bromo-benzyl)-methyl-amine

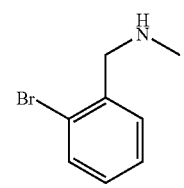

(1A)

A solution of 2-bromobenzylbromide (9 g, 36.1 mmol) in MeOH (60 ml) was added dropwise over 30 min. to a solution of methylamine in MeOH (200 mL of a 2.0 M solution, 0.4 mol). The resulting solution was stirred at rt for 2 h and concentrated. The residue obtained was dissolved in DCM (100 mL) and successively washed with saturated aqueous sodium carbonate, dried over sodium sulphate, and concentrated. The resulting oil was distilled to afford the title compound (7 g, 95%) as a colorless oil (b.p. 110° C. at 0.1 mm Hg, LC/MS retention time=1.22 min.; M$^+$ Part B. {[(2-Bromo-benzyl)-methyl-carbamoyl]-methyl}-carbamic acid tert-butyl ester =201.92, Column: Phenominex 4.6 mm×50 mm. Solvent A=10% MeOH, 90% H$_2$O, 10 mM NH4Ac; Solvent B=90% MeOH, 10% H$_2$O, 10 nM NH4Ac, Flow rate: 4 mL/min, Gradient: 0%B–100%B 4 min.).

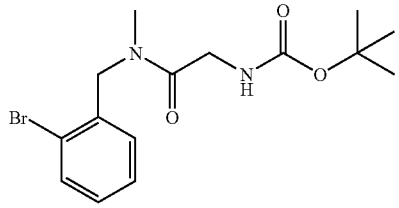

(1B)

To a solution of compound 1A (1.0 g, 5 mmol) in 50 mL of DCM was added N-Boc-glycine (950 mg, 5.4 mmol), followed by 1-hydroxy-7-azabenzotriazole (800 mg, 5.84 mmol) and 1-(3-dimethylaminopropyl)-3-ethylcarbodiimide hydrochloride (4.41 g, 7.38 mmol). The reaction mixture was stirred at rt for 4 hours and concentrated under reduced pressure. The resulting oil was dissolved in EtOAc and washed successively with saturated sodium bicarbonate, 1N-hydrochloric acid, dried over sodium sulfate and concentrated under reduced pressure to give the title compound (1.8 g, 99%) as a colorless oil, which was used for the subsequent step without further purification.

Part C. ({[2-(1-Ethoxy-vinyl)-benzyl]-methyl-carbamoyl}-methyl)-carbamic acid tert-butyl ester

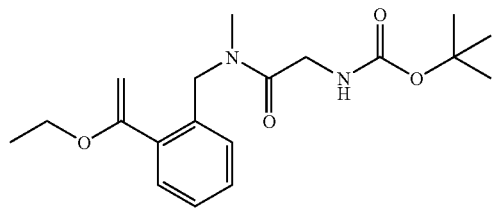

(1C)

To a solution of compound 1B (1.0 g, 2.79 mmol) in 50 mL of dioxane was added tributyl(1-ethoxyvinyl)tin (0.976 mL, 2.70 mmol) and dichlorobis(triphenyl-phosphine)palladium(II) (0.160 g, 0.16 mmol). The reaction mixture was equipped with a reflux condenser and heated at 100° C. for 18 hours. More dichlorobis-(triphenylphosphine)palladium (II) (0.100 g, 0.10 mmol) was added and the mixture was heated at 100° C. for another 2 h. The mixture was cooled to rt, concentrated under reduced pressure and the residue obtained was taken up in EtOAc. A solution of saturated potassium fluoride was added, and the resulting mixture was filtered over a thin pad of Celite® into a separating funnel. The filtrate was washed successively with saturated potassium fluoride and water, then dried over sodium sulfate, and concentrated under reduced pressure. The resulting oil was purified by silica gel column chromatography to yield the title compound as an oil (0.820 g, 84%) (LC/MS retention time=3.61 min.; M$^+$=349, Column: Phenominex 4.6 mm×50 mm, Solvent A=10% MeOH, 90% H$_2$O, 10 mM NH4Ac; Solvent B=90% MeOH, 10% H$_2$O, 10 nM NH4Ac, Flow rate: 4 mL/min, Gradient: 0%B–100%B 4 min.).

Part D. ({[2-(2-Azido-acetyl)-benzyl]-methyl-carbamoyl}-methyl)-carbamic acid tert-butyl ester

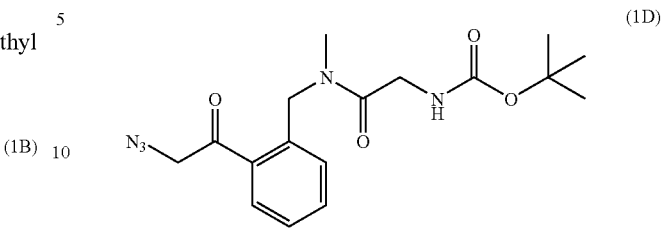

(1D)

To a solution of compound 1C (3.6 g, 10.3 mmol) in THF (30 mL) and water (5 mL) was added N-bromosuccinimide (2.0 g, 11.23 mmol) and the contents stirred at rt for 10 min. The solution was concentrated under reduced pressure and partitioned between DCM and water. The DCM layer was dried over sodium sulfate, concentrated under reduced pressure to yield ({[2-(2-Bromo-acetyl)-benzyl]-methyl-carbamoyl}-methyl)-carbamic acid tert-butyl ester, which was then dissolved in a mixture of acetone (20 mL) and water (5 mL). Sodium azide (0.737 g, 11.16 mmol) was added and the reaction mixture stirred at 50° C. for 10 min., concentrated under reduced pressure, and partitioned between DCM and water. The DCM layer was dried over sodium sulfate and concentrated under reduced pressure. The resulting oil was purified by silica gel column chromatography to yield the title compound as a yellow oil (2.56 g, 68%) (LC/MS retention time=2.90 min.; M$^+$=363, Column: Phenominex 4.6 mm×50 mm, Solvent A=10% MeOH, 90% H$_2$O, 10 mM NH4Ac; Solvent B=90% MeOH, 10% H$_2$O, 10 nM NH4Ac, Flow rate: 4 mL/min, Gradient: 0%B–100% B 4 min.).

Part E. 4-Nitro-2-methoxy-((α,α bisacetoxy)toluene

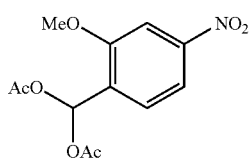

(1E)

To a 5 L three-necked round bottom flask equipped with a mechanical stirrer was added 4-nitro-2-methoxytoluene (150.0 g, 0.8973 mol), HOAc (900 mL) and Ac$_2$O (900 mL). The mixture was stirred and cooled to 8° C. with an acetone/ice bath. Concentrated H$_2$SO$_4$ (136 mL) was carefully added while keeping the reaction temperature below 19° C. After cooling to 0° C., CrO$_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to give compound 1E (129.0 g, 51%). $^1$H NMR (CDCl$_3$) d 8.02 (s, 1H), 7.89 (d, J=8.4 Hz, 1H), 7.77 (s, 1H), (d, 8.4 Hz, 1H), 3.98 (s; 3H), 2.16 (s, 6H).

Part F. 4-Nitro-2-methoxybenzaldehyde

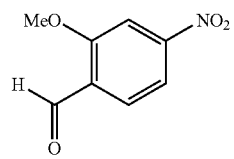

(1F)

To a 2 L rounded bottom flask equipped with a condenser and a mechanical stirrer was placed compound 1E (250.7 g, 0.8851 mol), dioxane (300 mL) and concentrated HCl (60 mL). The reaction mixture was heated to reflux and stirred under $N_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give compound 1F (146.3 g, 91%) as a yellow solid. $^1$H NMR (CDCl$_3$) d 10.54 (s, 1H), 8.00 (d, J=8.3 Hz, 1H), 7.91 (s, 1H), 7.89 (d, J=8.3 Hz, 1H), 4.08 (s, 3H).

Part G. 5-(4-Nitro-2-methoxyphenyl)oxazole

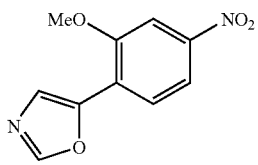

(1G)

To a 5 L three-necked round bottom flask equipped with a condenser and a mechanical stirrer was placed compound 1F (146.3 g, 0.8076 mol), tosylmethyl isocyanide (157.7 g, 0.8077 mol), $K_2CO_3$ (116.6 g, 0.8075 mol) and MeOH (2.5 L). The mixture was heated to reflux under $N_2$ and stirred for 3 hours. Water (1.25 L) was added drop-wise while maintaining the pot temperature between 59–69° C. The resulting slurry was cooled to rt, and then to 5° C. with an ice-water bath. After stirring for 30 minutes at 5° C, the slurry was filtered. The resulting cake was washed with water (3×400 mL) and dried in a vacuum oven at 45° C. for 20 hours to compound 1G (148.5 g, 84%) as a yellow-reddish solid. $^1$H NMR (CDCl$_3$) d 8.02 (s, 1H), 7.97 (d, J=2 Hz, 1H), 7.95 (d, J=2 Hz, 1H), 7.86 (s, 1H), 7.78 (s, 1H), 4.11 (s, 3H).

Part H. 5-(4-Amino-2-methoxyphenyl)oxazole

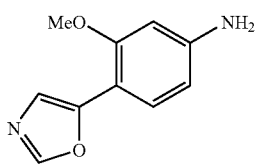

(1H)

In a 2 L hydrogenation flask was placed compound 1G (130.0 g, 0.6131 mol), Pd/C (10%, 26.2 g) and absolute EtOH (1280 mL). The mixture was hydrogenated at 35–45 psi $H_2$ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at rt, the slurry was filtered. The cake was washed with heptane (3×100 mL) and air-dried to give 1H (80.0 g). A second portion of product (30.2 g) was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

Part I. 5-(4-Isothiocyanato-2-methoxy-phenyl)-oxazole

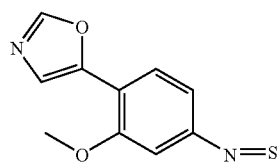

(1I)

To a solution of 5-(4-Amino-2-methoxyphenyl)oxazole 1H (200 mg, 1.05 mmol) in DCM (2 mL) was added thiocarbonyldiimizaole (224 mg, 1.26 mmol) and the mixture was stirred at rt for 3 h. The mixture was concentrated under reduced pressure, and the residue was dissolved in MeOH (9 mL) and aliquots of 3 mL were filtered through an SCX cartridge (CUBX1HL, 500 mg cartridge, United Chemical Technologies, Bristol Pa., USA). The filtrate was concentrated under reduced pressure to afford 440 mg of the title compound which was used for the subsequent step without further purification.

Part J. Example 1

To a solution of compound 1D (0.180 g, 0.50 mmol) in 2 mL of dioxane was added compound 1I (220 mg of crude mixture, 1 mmol) followed by triphenylphosphine (0.140 g, 0.53 mmol). The reaction mixture was placed in an oil bath preheated to 80° C. and stirred for 2 hour, then cooled to rt and the solvent was evaporated. The residue was treated for 1 h at rt with a 1:1 mixture of TFA and DCM, and the mixture was concentrated under reduced pressure. The residue was dissolved in MeOH (2 mL), loaded onto an SCX cartridge (CUBX1HL, 500 mg cartridge, United Chemical Technologies, Bristol Pa., USA) which was washed with MeOH (3 mL). The title compound was eluted from the cartridge with a 2.0 M solution of ammonia in MeOH (3mL) and purified by preparative reverse phase HPLC to yield 0.070 g of an orange oil. (LC/MS retention time=2.93 min.; MH$^+$=435, Column: Phenominex 4.6 mm×50 mm, Solvent A=10% MeOH, 90% $H_2O$, 10 mM NH4Ac; Solvent B=90% MeOH, 10% $H_2O$, 10 mM NH4Ac, Flow rate: 4 mL/min, Gradient: 0%B–100%B 4 min.).

EXAMPLES 2–29

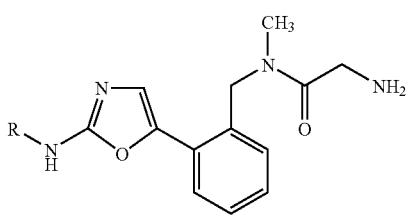

Compounds having the above formula, wherein the group R has the values listed in Table 1, were prepared following the procedure set forth above for Example 1, using appropriately-substituted aryl or heteroaryl amine in place of 5-(4-Amino-2-methoxyphenyl)oxazole 1H.

TABLE 1

| Ex. | R | HPLC time (min) | HPLC Method | MH+ |
|---|---|---|---|---|
| 2 | (1-methylnaphthalenyl) | 2.57 | c | 387.3 |
| 3 | (phenoxy-p-tolyl) | 3.11 | c | 429.3 |
| 4 | (benzyloxy-m-tolyl) | 3.17 | c | 443.32 |
| 5 | (oxazol-5-yl-p-tolyl) | 2.61 | c | 404.29 |
| 6 | (2-methoxy-4-methylbiphenyl) | 3.26 | b | 443.23 |
| 7 | (2-chloro-4-methylphenyl-oxazole) | 3.02 | b | 438.15 |
| 8 | (1,2,4-oxadiazol-3-yl-p-tolyl) | 2.68 | b | 405.21 |
| 9 | (1H-tetrazol-5-yl-p-tolyl) | 2.44 | b | 405.21 |
| 10 | (isothiazol-4-yl-p-tolyl) | 2.75 | b | 420.21 |

TABLE 1-continued

| Ex. | R | HPLC time (min) | HPLC Method | MH+ |
|---|---|---|---|---|
| 11 | (oxazol-5-yl-m-tolyl) | 2.67 | b | 404.21 |
| 12 | (2-methylnaphthalenyl) | 3.02 | b | 387.21 |
| 13 | (2-methyl-5-methylbenzothiazole) | 2.7 | b | 408.18 |
| 14 | (5-methyl-1H-benzimidazole) | 1.93 | b | 377.16 |
| 15 | (1H-imidazol-4-yl-p-tolyl) | 2.08 | b | 403.22 |
| 16 | (2-furyl-5-methylbenzoxazole) | 2.92 | b | 444.19 |
| 17 | (2-chloro-4-methylphenyl-thiazole) | 3.21 | a | 453.81 |
| 18 | (2-ethyl-4-methylphenyl-oxazole) | 3.11 | a | 431.98 |

TABLE 1-continued

| Ex. | R | HPLC time (min) | HPLC Method | MH+ |
|---|---|---|---|---|
| 19 | 2-(oxazol-2-yl)-3-methoxy-4-methylphenyl | 2.86 | a | 433.95 |
| 20 | 2-(4-methyloxazol-2-yl)-4-methylphenyl | 3.12 | a | 418 |
| 21 | 2-(5-methyloxazol-2-yl)-4-methylphenyl | 3.12 | a | 418 |
| 22 | 4-(imidazol-1-yl)phenyl | 2.65 | a | 403.02 |
| 23 | 4-(1-methylpyrazol-5-yl)phenyl | 2.88 | a | 417.03 |
| 24 | 1-methyl-3-cyano-6-methylindol-yl | 2.79 | a | 415.01 |
| 25 | 4-(1,2,3-thiadiazol-4-yl)phenyl | 2.68 | b | 421.23 |
| 26 | 3-(1-methyl-4-bromopyrazol-3-yl)-4-methylphenyl | 2.99 | b | 495.18 |
| 27 | 5-methylindazol-yl | 2.05 | b | 377.2 |
| 28 | 4-(5-trifluoromethylpyrazol-1-yl)phenyl | 3.12 | b | 471.2 |
| 29 | 5-methyl-2-oxo-benzimidazolyl | 1.87 | b | 393.17 |

HPLC Conditions for Table 1:

[a]Column: Phenominex 4.6 × 5.0 mm. Solvent A = 10% MeOH, 90% H$_2$O, 10 mM NH4Ac; Solvent B = 90% MeOH, 10% H$_2$O, 10 mM NH4Ac. Flow rate: 4 mL/min. Gradient: 4 min 0% B–100% B.

[b]Column: Phenominex ODS 4.6 × 5.0 mm. Solvent A = 10% MeOH, 90% H$_2$O, 0.1% TFA; Solvent B = 90% MeOH, 10% H$_2$O, 0.1% TFA. Flow rate: 4 mL/min. Gradient: 4 min 0% B–100% B.

[c]Column: Phenominex Luna C18 4.6 × 5.0 mm. Solvent A = 10% MeOH, 90% H$_2$O, 0.1% TFA; Solvent B = 90% MeOH, 10% H$_2$O, 0.1% TFA. Flow rate: 4 mL/min. Gradient: 4 min 0% B–100% B.

EXAMPLES 30–48

Compounds having the formulae set forth in Table 2, were prepared following the same or similar procedures to those set forth above for Examples 1–29, and/or in the general schemes previously set forth herein. In the compounds shown in Table 2, the terminal nitrogen atom on the right-hand side is intended to designate NH$_2$ and the central nitrogen atom NH. These compounds are useful in the inventive methods of inhibiting Factor VIIa.

TABLE 2
| Ex. | Structure |
|---|---|
| 30 | 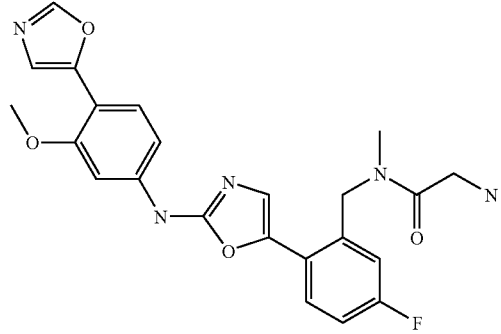 |
| 31 | 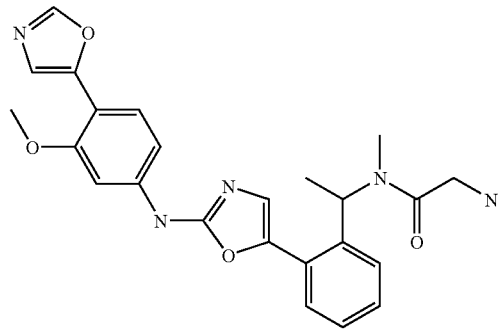 |
| 32 | 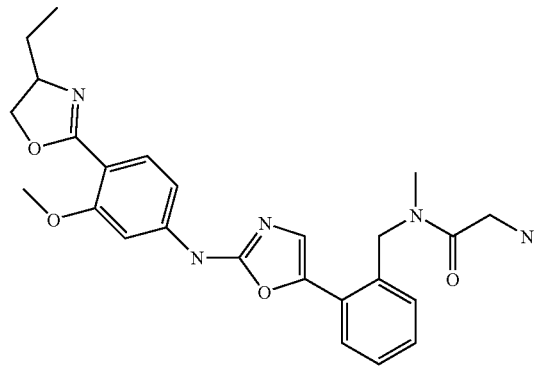 |
| 33 | 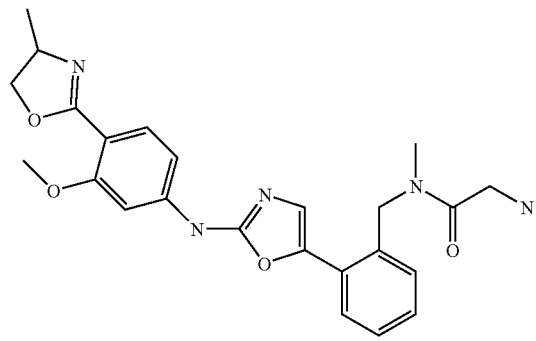 |

TABLE 2-continued
| Ex. | Structure |
|---|---|
| 34 | 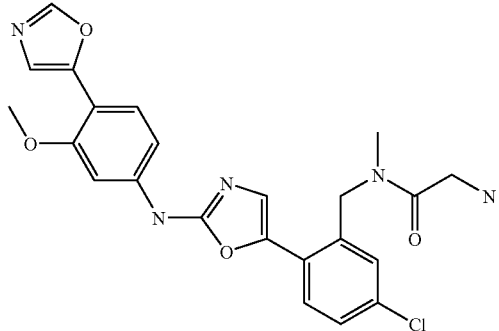 |
| 35 | 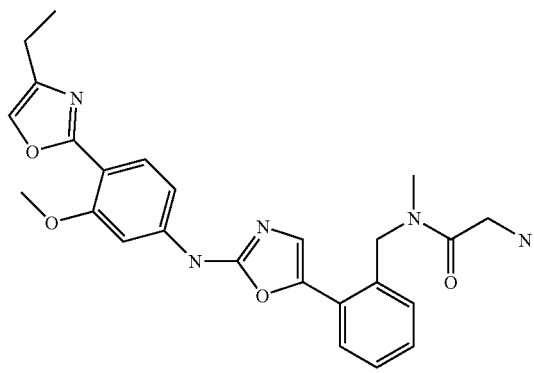 |
| 36 | 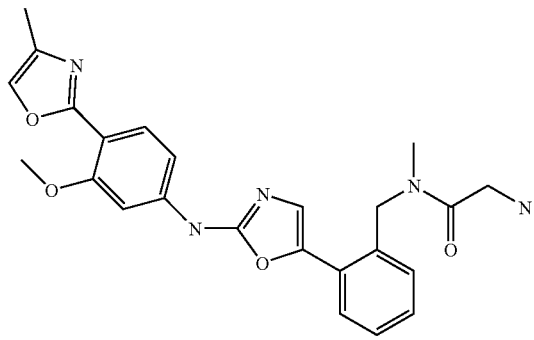 |
| 37 | 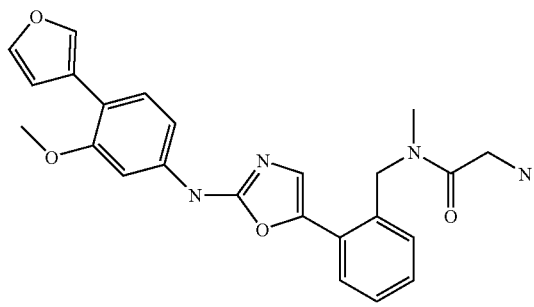 |

TABLE 2-continued
| Ex. | Structure |
|---|---|
| 38 | 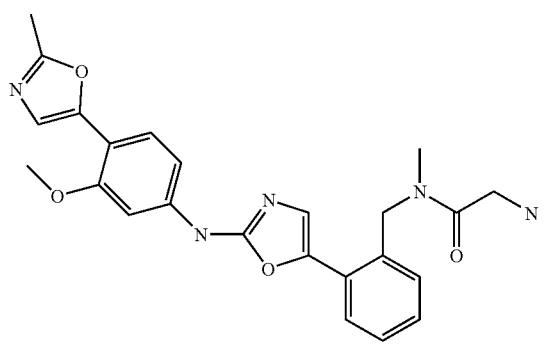 |
| 39 | 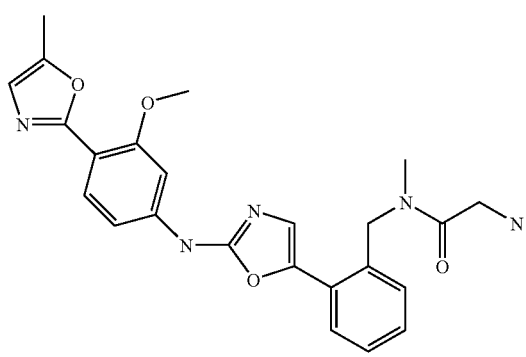 |
| 40 | 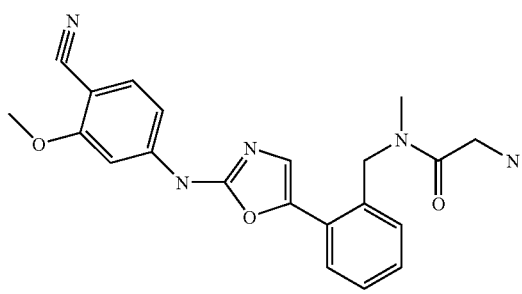 |
| 41 | 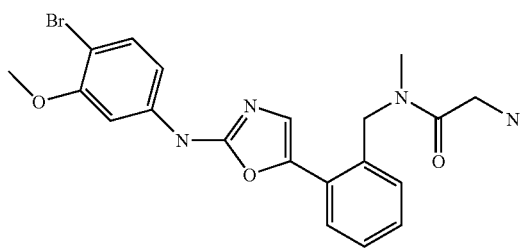 |
| 42 | 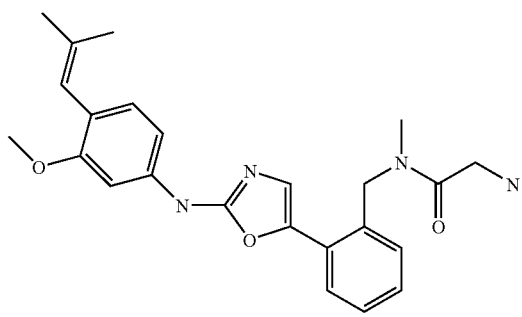 |

TABLE 2-continued
| Ex. | Structure |
|---|---|
| 43 | 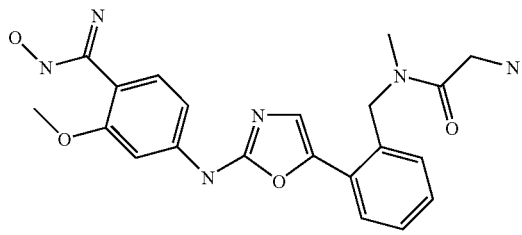 |
| 44 | 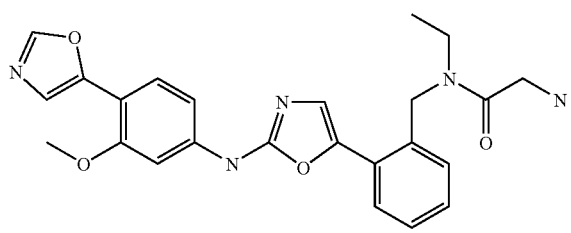 |
| 45 | 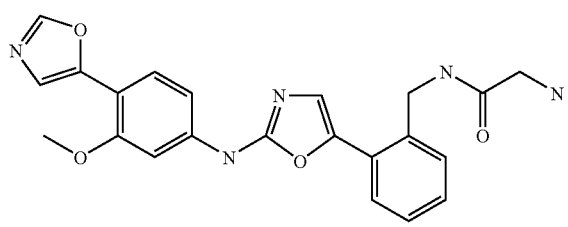 |
| 46 | 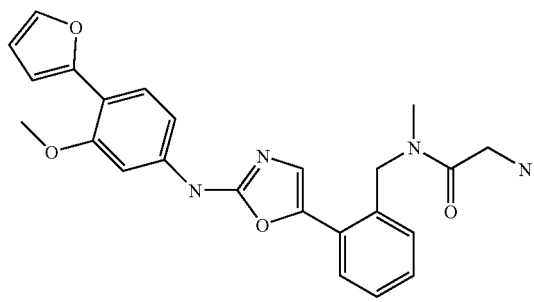 |
| 47 | 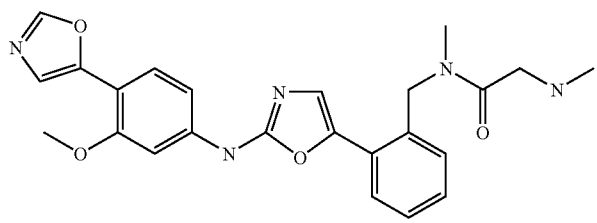 |
| 48 | 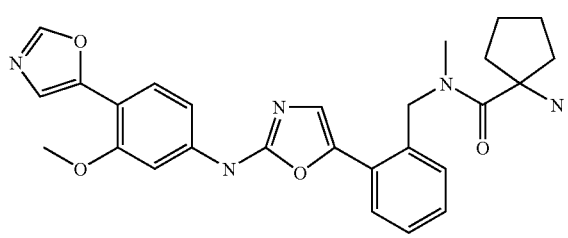 |

We claim:

1. A method of treating a disorder selected from myocardial infarction, unstable angina, thromboembolic stroke, venous thrombosis, pulmonary embolism, peripheral occlusive arterial disease, atherosclerotic vascular disease, atheraclerotic plaque rupture, and/or thromboembolic consequences of surgery, in a mammal comprising administering to the mammal in need of treatment thereof an effective amount of at least one compound having the formula (I),

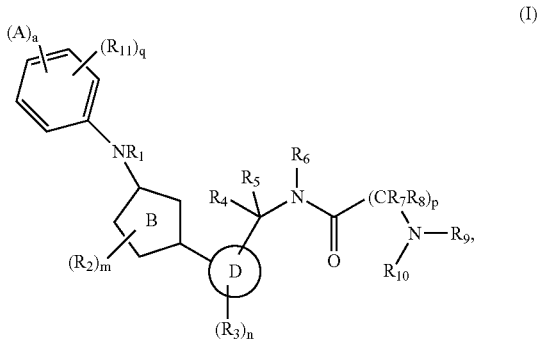

(I)

or a pharmaceutically-acceptable salt, hydrate or prodrug thereof, wherein:

A is a five or six-membered saturated or unsaturated carbocyclic, heterocyclic or heteroaryl ring, said ring A being optionally substituted with up to three groups selected from $R_{27}$;

B is

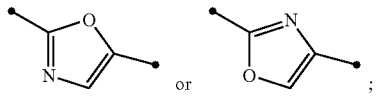

D is phenyl or cycloalkyl;

$R_1$ is hydrogen, $C_{1-4}$alkyl, or $C_{1-4}$alkyl substituted with one to two $R_{21}$;

$R_2$ and $R_3$ are attached to any available carbon atom of ring B and ring D, respectively, and at each occurrence are independently selected from halogen, cyano, $NO_2$, $C_{1-6}$alkyl, substituted $C_{1-6}$alkyl, $C_{2-6}$alkenyl, $C_{2-6}$alkynyl, haloalkyl, haloalkoxy, —)$OR_{15}$, —C(=O)$R_{15}$, —OC(=O)$R_{15}$, —CO$_2R_{15}$, —OCO$_2R_{15}$, —C(=O)NR$_{15}R_{16}$, —OC(=O)NR$_{15}R_{16}$, —NR$_{15}R_{16}$, —NR$_{16}$C(=O)$R_{15}$, —NR$_{16a}$C(=O)NR$_{15}R_{16}$, —NR$_{16}$CO$_2R_{15}$, —SR$_{15}$, —S(O)$R_{15}$, —SO$_2R_{15}$, —SO$_2$NR$_{15}R_{16}$, —SO$_3R_{15}$, —NR$_{16}$SO$_2R_{15}$, and —NR$_{16a}$SO$_2$NR$_{15}R_{16}$;

$R_4$ and $R_5$ are independently selected from hydrogen, halogen, hydroxy, cyano, $C_{1-3}$alkoxy, —OCF$_3$, CF$_3$, amino, $C_{1-6}$alkylamino, $C_{1-4}$alkyl, and $C_{1-4}$alkyl substituted with one to two $R_{22}$, or alternatively, $R_4$ and $R_5$ taken together may from a 3–8 membered cycloalkyl or heterocyclic spiro ring, said ring being optionally substituted with up to three $R_{28}$;

$R_6$ is selected from hydrogen, $C_{1-4}$alkyl, and $C_{1-4}$alkyl substituted with one to two $R_{23}$;

$R_7$ and $R_8$ are independently selected from hydrogen, halogen, hydroxy, cyano, $C_{1-3}$alkoxy, —OCF$_3$, CF$_3$, amino, $C_{1-6}$alkylamino, $C_{1-4}$alkyl, and $C_{1-4}$alkyl substituted with one to two $R_{24}$; or alternatively, $R_7$ and $R_8$ taken together may form a 3–8 membered cycloalkyl or heterocyclic spiro ring, said ring being optionally substituted with up to three $R_{29}$; or alternatively, one or both of $R_7$ and $R_8$ may be taken together with one or both of $R_9$ and $R_{10}$ to form a heterocyclic or heteroaryl ring, said ring in turn being optionally substituted with up to three $R_{30}$;

$R_9$ and $R_{10}$ are independently selected from hydrogen, $C_{1-4}$alkyl, and $C_{1-4}$alkyl substituted with one to two $R_{25}$; or alternatively, $R_9$ and $R_{10}$ taken together may form a 3–8 membered heterocyclic ring or a five to six membered heteroaryl ring, said ring being optionally substituted with up to three $R_{30}$; or alternatively, one or both of $R_9$ and $R_{10}$ may be taken together with one or both of $R_7$ and $R_8$ to form a heterocyclic or heteroaryl ring optionally substituted with up to three $R_{30}$;

$R_{11}$ at each occurrence is independently selected from halogen, cyano, $NO_2$, $C_{1-6}$alkyl, substituted $C_{1-6}$alkyl, $C_{2-6}$alkenyl, $C_{2-6}$alkynyl, haloalkyl, haloalkoxy, —OR$_3$, —C(=O)$R_{13}$, —OC(=O)$R_{13}$, —CO$_2R_{13}$, —OCO$_2R_{13}$, —C(=O)NR$_{13}R_{14}$, —OC(=O)NR$_{13}R_{14}$, —NR$_{13}R_{14}$, —NR$_{14}$C(=O)$R_{13a}$, —NR$_{14}$CO$_2R_{13}$, —SR$_{13}$, —S(O)$R_{13}$, —SO$_2R_{13}$, —SO$_2$NR$_{13}R_{14}$, —SO$_3R_{13}$, —NR$_{14}$SO$_2R_{13}$, and —NR$_{14a}$SO$_2$NR$_{13}R_{14}$ or alternatively, two $R_{11}$ groups may be taken together to form a fused benzo, heteroaryl, or heterocyclic ring, wherein said ring in turn is optionally substituted with up to one A group and/or one to two $R_{31}$; provided, however, that $R_{11}$ is not alkyl substituted with —NR$_{18a}$C(=O)NR$_{17}R_{18}$;

$R_{13}$, $R_{14}$, and $R_{14a}$ at each occurrence independently of each other are selected from hydrogen, $C_{1-6}$alkyl, substituted $C_{1-6}$alkyl, $C_{2-8}$alkynyl, $C_{2-8}$alkynyl, $C_{3-10}$cycloalkyl($C_{0-4}$alkyl), aryl($C_{0-4}$alkyl), heterocyclo($C_{0-4}$alkyl), and heteroaryl($C_{0-4}$alkyl), wherein each of said cycloalkyl, aryl, heterocyclo, and heteroaryl groups are optionally substituted with up to two substituents independently selected from $R_{32}$; provided, however, that when $R_{13}$ is attached to a sulfonyl group as in SO$_2R_{13}$, S(=O)$R_{13}$, and SO$_3R_{13}$, then $R_{13}$ is not hydrogen; or alternatively, $R_{13}$ and $R_{14}$ can be taken together with the nitrogen atom to which they are attached to form a heterocyclo or heteroaryl, said ring being in turn optionally substituted with up to three groups selected from $R_{32}$;

$R_{13a}$ is selected from hydrogen, $C_{1-6}$alkyl, substituted $C_{1-6}$alkyl, $C_{2-8}$alkenyl, $C_{2-8}$alkynyl, $C_{3-10}$cycloalkyl ($C_{0-4}$alkyl), aryl($C_{0-4}$alkyl), heterocyclo($C_{1-4}$alkyl), and heteroaryl($C_{1-4}$alkyl), wherein each of said cycloalkyl, aryl, heterocyclo, and heteroaryl groups are optionally substituted wit up to two substituents independently selected from $R_{32}$;

$R_{15}$ at each occurrence independently of each other $R_{15}$ is selected from hydrogen, $C_{1-6}$alkyl, substituted $C_{1-6}$alkyl, $C_{2-8}$alkenyl, $C_{2-8}$alkynyl, $C_{3-10}$cycloalkyl ($C_{0-4}$alkyl), aryl($C_{0-4}$alkyl), heterocyclo($C_{0-4}$alkyl), and heteroaryl($C_{0-4}$alkyl), wherein each of said cycloalkyl, aryl, heterocyclo, and heteroaryl groups are optionally substituted with up to two substituents independently selected from $R_{33}$; provided, however, that when $R_{15}$ is attached to a sulfonyl group as in SO$_2R_{15}$, S(=O)$R_{15}$, and SO$_3R_{15}$, then $R_{15}$ is not hydrogen; and $R_{16}$ and $R_{16a}$ at each occurrence independently of each other $R_{16}$ and $R_{16a}$ are selected from hydrogen, $C_{1-6}$alkyl, substituted $C_{1-6}$alkyl, $C_{2-6}$alkenyl, $C_{2-6}$alkynyl, —$OR_{19}$, —C(=O)$R_{19}$, —$CO_2R_{19}$, —$SO_2R_{19}$, $C_{3-10}$cycloalkyl($C_{0-4}$alkyl), aryl($C_{0-4}$alkyl), heterocyclo($C_{0-4}$alkyl), and heteroaryl($C_{0-4}$alkyl), wherein $R_{19}$ is $C_{1-6}$alkyl, $C_{3-10}$cycloalkyl, aryl, heterocyclo, or heteroaryl, and each of said $R_{19}$, cycloalkyl, aryl, heterocyclo, and heteroaryl groups are in turn optionally substituted with up to two substituents independently selected from $R_{34}$;

alternatively, $R_{15}$ and $R_{16}$ can be taken together with the nitrogen atom to which they are attached to form a heterocyclo or heteroaryl, said ring being in turn optionally substituted with up to three groups selected from $R_{34}$;

$R_{17}$ and $R_{18}$ is are independently selected from hydrogen, alkyl, substituted alkyl, cyano, hydroxy, alkoxy, cycloalkyl, heterocyclo, aryl and heteroaryl, or taken together may form a heteroaryl or heterocyclo ring;

$R_{17a}$ is hydrogen, alkyl, or substituted alkyl;

$R_{21}$, $R_{22}$, $R_{23}$, $R_{24}$, $R_{25}$, and $R_{26}$ are independently selected from halogen, cyano, hydroxy, $C_{1-3}$alkoxy, $OCF_3$, $CF_3$, amino, and $C_{1-6}$alkylamino;

$R_{27}$, $R_{28}$, $R_{29}$, $R_{30}$, $R_{31}$, $R_{32}$, $R_{33}$, and $R_{34}$ are at each occurrence independently selected from $C_{1-4}$alkyl, $C_{2-6}$alkenyl, $C_{2-6}$alkynyl, oxo (=O), halo($C_{0-4}$alkyl), $NO_2$($C_{0-4}$alkyl), hydroxy($C_{0-4}$alkyl), $CF_3$($C_{0-4}$alkyl), $OCF_3$($C_{0-4}$alkyl), cyano($C_{0-4}$alkyl), amino($C_{0-4}$alkyl), $C_{1-4}$alkoxy($C_{0-4}$alkyl), —$C_{1-6}$alkylamino($C_{0-4}$alkyl), $C_{1-4}$alkylthio($C_{0-4}$alkyl), carbamyl($C_{0-4}$alkyl, —C(=O)$C_{1-4}$alkyl, —$CO_2C_{1-4}$alkyl, —S(O)($C_{1-4}$alkyl), —$SO_2$($C_{1-4}$alkyl), —$SO_2NH_2$, —$SO_2NH$($C_{1-4}$alkyl), —$SO_3H$, —$SO_3$($C_{1-4}$alkyl), —NHCO($C_{1-6}$alkyl), and —C(=O)NH($C_{1-4}$alkyl), provided, however, that when $R_{26}$, $R_{27}$, $R_{30}$, $R_{31}$, $R_{32}$, $R_{33}$, and $R_{34}$ are substituents attached to an aryl or heteroaryl ring, said groups are not selected from oxo (=O); provided further, that when $R_{26}$, $R_{27}$, $R_{30}$, $R_{31}$, $R_{32}$, $R_{33}$, and $R_{34}$ are hydroxy and attached to an aryl or heteroaryl ring, the ring may undergo tautomerization to an oxo species, or exist as an equilibrium mixture of both tautomers;

a is 0 or 1;
m is 0, 1, or 2;
n is 0, 1, 2, 3, or 4;
p is 0, 1 or 2; and
q is 0, 1, 2, 3 or 4.

2. The method according to claim 1, comprising administering to the mammal a compound having the formula (Ib),

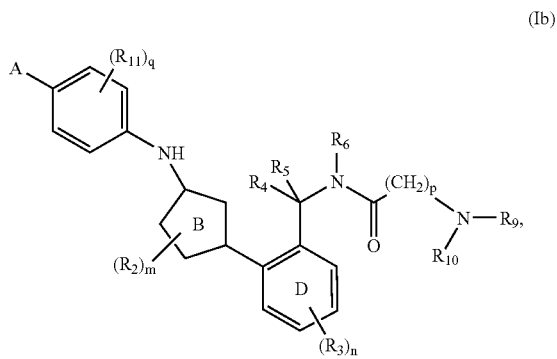

(Ib)

or a pharmaceutically-acceptable salt, hydrate or prodrug thereof, wherein:

B is

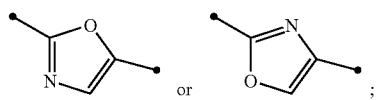

$R_2$ and $R_3$ are attached to any available carbon atom of ring B and ring D, respectively, and at each occurrence are independently selected from halogen, cyano, $C_{1-4}$alkyl, hydroxy($C_{1-4}$alkyl), $CF_3$($C_{0-4}$alkyl), $OCF_3$($C_{0-4}$alkyl), cyano($C_{1-4}$alkyl), amino($C_{0-4}$alkyl), $C_{1-4}$alkoxy($C_{0-4}$alkyl), $C_{1-6}$alkylamino($C_{0-4}$alkyl), and $C_{1-4}$alkylthio($C_{0-4}$alkyl);

$R_4$ and $R_5$ are independently selected from hydrogen and $C_{1-4}$alkyl;

$R_6$ is selected from $C_{1-4}$alkyl;

$R_9$ and $R_{10}$ are independently selected from hydrogen, $C_{1-4}$alkyl, and $C_{1-4}$alkyl substituted with one to two $R_{25}$; or alternatively, $R_9$ and $R_{10}$ taken together may form a 3–8 membered heterocyclic ring or a five to six membered heteroaryl ring, said ring being optionally substituted with up to three $R_{30}$;

$R_{11}$ at each occurrence is independently selected from halogen, cyano, $C_{1-4}$alkyl, hydroxy($C_{0-4}$alkyl), $CF_3$($C_{0-4}$alkyl), $OCF_3$($C_{0-4}$alkyl), cyano($C_{1-4}$ alkyl), amino($C_{0-4}$alkyl), $C_{1-4}$alkoxy($C_{0-4}$alkyl), $C_{1-6}$alkylamino ($C_{0-4}$ alkyl), and $C_{1-4}$ alkylthio($C_{0-4}$alkyl), or two $R_{11}$ groups may be taken together to form a fused benzo, heteroaryl, or heterocyclic ring, wherein said ring in turn is optionally substituted with a group A or one to two of $C_{1-4}$alkyl, oxo(=O), halogen, cyano, trifluoromethyl, or trifluoromethoxy;

$R_{30}$ at each occurrence is independently selected from $C_{1-4}$alkyl, oxo (=O), halo($C_{0-4}$alkyl), hydroxy($C_{0-4}$ alkyl), $CF_3$($C_{0-4}$alkyl), $OCF_3$($C_{0-4}$alkyl), cyano($C_{0-4}$ alkyl), amino($C_{0-4}$alkyl), $C_{1-4}$alkoxy($C_{0-4}$alkyl), $C_{1-6}$alkylamino($C_{0-4}$alkyl), $C_{1-4}$alkylthio($C_{0-4}$alkyl), —C(=O)$C_{1-4}$alkyl, and —$CO_2C_{1-4}$alkyl;

m is 0 or 1; and
q is 0, 1, or 2.

3. The method according to claim 1, comprising administering to the mammal a compound of formula (I), or a pharmaceutically-acceptable salt, hydrate or prodrug thereof, wherein:

A is selected from phenyl, oxazolyl, thiazolyl, isothiazolyl, imidazolyl, furyl, thienyl, thiadiazolyl, oxadiazolyl, tetrazolyl, triazolyl, diazolyl, pyrrolyl, and pyrazolyl, said ring A being optionally substituted with up to two groups selected from halogen, $C_{1-4}$alkyl, haloalkyl, haloalkoxy, OH, $C_{1-4}$alkoxy, $C_{1-4}$alkylcarbonyl, CN, $NH_2$, NH($C_{1-4}$alkyl), and N(alkyl)$_2$; and
a is 1.

4. The method according to claim 1, comprising administering to the mammal a compound of formula (I), or a pharmaceutically-acceptable salt, hydrate or prodrug thereof, wherein:

B is

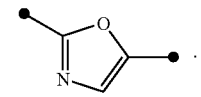

5. The method according to claim 4, comprising administering to the mammal a compound of formula (I), or a pharmaceutically-acceptable salt, hydrate or prodrug thereof, wherein m is 0.

6. The method according to claim 1, comprising administering to the mammal a compound of formula (I), or a pharmaceutically-acceptable salt, hydrate or prodrug thereof, in which $R_3$ is selected from $C_{1-4}$alkyl and halogen, or n is 0.

7. The method according to claim 1, comprising administering to the mammal a compound of formula (I), or a pharmaceutically-acceptable salt, hydrate or prodrug thereof, in which D is phenyl.

8. The method according to claim 1, comprising administering to the mammal a compound of formula (I), or a pharmaceutically-acceptable salt, hydrate or prodrug thereof, in which $R_4$ and $R_5$ are hydrogen or $C_{1-4}$alkyl.

9. The method according to claim 1, comprising administering to the mammal a compound of formula (I), or a pharmaceutically-acceptable salt, hydrate or prodrug thereof, in which $R_6$ is $C_{1-4}$alkyl.

10. The method according to claim 1, comprising administering to the mammal a compound of formula (I), or a pharmaceutically-acceptable salt, hydrate or prodrug thereof, in which $R_7$ and $R_8$ are hydrogen or $C_{1-4}$alkyl.

11. The method according to claim 1, comprising administering to the mammal a compound of formula (I), or a pharmaceutically-acceptable salt, hydrate or prodrug thereof, in which $R_9$ and $R_{10}$ are hydrogen or $C_{1-4}$alkyl.

12. A method of treating a disorder selected from myocardial infarction, unstable angina, thromboembolic stroke, venous thrombosis, pulmonary embolism, peripheral occlusive arterial disease, atherosclerotic vascular disease, atheraclerotic plaque rupture, and/or thromboembolic consequences of surgery, in a mammal comprising administering to the mammal in need of treatment thereof an effective amount of a compound having the formula (Ia),

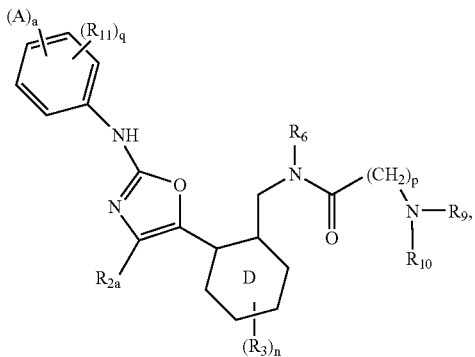

(Ia)

or a pharmaceutically-acceptable salt, hydrate, or prodrug thereof, in which:

A is selected from phenyl, oxazolyl, thiazolyl, isothiazolyl, imidazolyl, furyl, thienyl, thiadiazolyl, oxadiazolyl, tetrazolyl, triazolyl, diazolyl, pyrrolyl, and pyrazolyl, said ring A being optionally substituted with up to two groups selected from halogen, $NO_2$, $C_{1-4}$alkyl, haloalkyl, haloalkoxy, OH, $C_{1-4}$alkoxy, $C_{1-4}$alkylcarbonyl, CN, $NH_2$, $NH(C_{1-4}$alkyl), and $N(alkyl)_2$;

D is phenyl;

$R_{2a}$ is selected from hydrogen, halogen, $C_{1-4}$alkyl, hydroxy($C_{0-4}$alkyl), $CF_3$($C_{0-4}$alkyl), $OCF_3$($C_{0-4}$alkyl), cyano($C_{0-4}$alkyl), amino($C_{0-4}$alkyl), $C_{1-3}$alkoxy($C_{0-4}$alkyl), and $C_{1-6}$alkylamino($C_{0-4}$alkyl);

$R_3$ is selected from hydrogen, halogen, $C_{1-4}$alkyl, hydroxy($C_{0-4}$alkyl), $CF_3$($C_{0-4}$alkyl), $OCF_3$($C_{0-4}$alkyl), cyano($C_{0-4}$alkyl), amino($C_{0-4}$alkyl), $C_{1-3}$alkoxy($C_{0-4}$alkyl), and $C_{1-6}$alkylamino($C_{0-4}$alkyl);

$R_{11}$ is selected from hydrogen, halogen, $C_{1-4}$alkyl, hydroxy($C_{0-4}$alkyl), $CF_3$($C_{0-4}$alkyl), $OCF_3$($C_{0-4}$alkyl), cyano($C_{0-4}$alkyl), amino($C_{0-4}$alkyl), $C_{1-3}$alkoxy($C_{0-4}$alkyl), and $C_{1-6}$alkylamino($C_{0-4}$alkyl), or two $R_{11}$ groups may be taken together to form a fused benzo, heteroaryl, or heterocyclic ring, wherein said ring in turn is optionally substituted with up to one A group and/or one to two $R_{31}$;

$R_6$ is $C_{1-4}$alkyl;

$R_9$ and $R_{10}$ are independently selected from hydrogen and $C_{1-4}$alkyl;

$R_{31}$ is selected from hydrogen, halogen, $C_{1-4}$alkyl, hydroxy($C_{0-4}$alkyl), $CF_3$($C_{0-4}$alkyl), $OCF_3$($C_{0-4}$alkyl), cyano($C_{0-4}$alkyl), and $C_{1-4}$alkoxy($C_{0-4}$alkyl);

a is 0 or 1;

n is 0, 1, 2, 3, or 4;

p is 0, 1 or 2; and q is 0, 1, or 2.

13. The method of claim 12, comprising administering to the mammal a compound of formula (Ia), wherein:

A is oxazolyl;

D is phenyl;

$R_{2a}$ is hydrogen, halogen, or $C_{1-4}$alkyl;

$R_3$ is hydrogen, halogen, or $C_{1-4}$alkyl; and p is 1.

14. The method of claim 13, comprising administering to the mammal a compound of formula (Ia), wherein:

$R_6$ is methyl; and $R_9$ and $R_{10}$ are hydrogen.

* * * * *

UNITED STATES PATENT AND TRADEMARK OFFICE
CERTIFICATE OF CORRECTION

PATENT NO.         : 7,041,692 B2                                              Page 1 of 1
APPLICATION NO. : 10/464366
DATED              : May 9, 2006
INVENTOR(S)        : Herpin et al.

It is certified that error appears in the above-identified patent and that said Letters Patent is hereby corrected as shown below:

On the TITLE page, item 75, "Inventors" should read:

Timothy Herpin, Princeton, NJ (US);
Gregory S. Bisacchi, Ringoes, NJ (US);
G. Murali Dhar, Newtown, PA (US)

Column 47, line 48, please delete "–)$OR_{15}$," and insert -- –$OR_{15}$,--

Signed and Sealed this

Twenty-third Day of January, 2007

JON W. DUDAS
*Director of the United States Patent and Trademark Office*